(12) United States Patent
Robek et al.

(10) Patent No.: US 9,987,353 B2
(45) Date of Patent: Jun. 5, 2018

(54) VIRUS LIKE VESICLES (VLVS) BASED VACCINES TO PREVENT OR TREAT CHRONIC HEPATITIS B VIRUS (HBV) INFECTION

(71) Applicants: YALE UNIVERSITY, New Haven, CT (US); Sandra E. Osborne, Granbury, TX (US)

(72) Inventors: Michael Robek, Slingerlands, NY (US); John Rose, Guilford, CT (US); Tracy Reynolds, New Haven, CT (US)

(73) Assignee: Yale University, New Haven, CT (US)

( * ) Notice: Subject to any disclaimer, the term of this patent is extended or adjusted under 35 U.S.C. 154(b) by 0 days. days.

(21) Appl. No.: 15/305,180

(22) PCT Filed: May 11, 2015

(86) PCT No.: PCT/US2015/030100
§ 371 (c)(1),
(2) Date: Oct. 19, 2016

(87) PCT Pub. No.: WO2015/175380
PCT Pub. Date: Nov. 19, 2015

(65) Prior Publication Data
US 2017/0056493 A1    Mar. 2, 2017

Related U.S. Application Data

(60) Provisional application No. 61/994,166, filed on May 16, 2014.

(51) Int. Cl.
| | |
|---|---|
| *A61K 39/00* | (2006.01) |
| *A61K 39/12* | (2006.01) |
| *A61K 39/21* | (2006.01) |
| *A61K 38/00* | (2006.01) |
| *A61K 39/205* | (2006.01) |
| *A61K 39/29* | (2006.01) |
| *C12N 15/86* | (2006.01) |

(52) U.S. Cl.
CPC ............ *A61K 39/292* (2013.01); *A61K 39/12* (2013.01); *C12N 15/86* (2013.01); *A61K 2039/5258* (2013.01); *A61K 2039/53* (2013.01); *A61K 2039/545* (2013.01); *A61K 2039/70* (2013.01); *C12N 2730/10134* (2013.01); *C12N 2730/10143* (2013.01); *C12N 2770/36143* (2013.01); *C12N 2810/6081* (2013.01)

(58) Field of Classification Search
CPC ............... A61K 39/0011; A61K 39/12; A61K 2039/5256; A61K 2300/00; C07K 14/005
See application file for complete search history.

(56) References Cited

U.S. PATENT DOCUMENTS

| | | |
|---|---|---|
| 2003/0099932 A1 | 5/2003 | Lorens et al. |
| 2010/0322965 A1 | 12/2010 | Rose et al. |
| 2011/0223197 A1 | 9/2011 | Vajdy et al. |

FOREIGN PATENT DOCUMENTS

WO    2015175382 A1    11/2015

OTHER PUBLICATIONS

International Search Report and Written Opinion for PCT International Application No. PCT/US2015/030100 dated Aug. 17, 2015.
Novella, et al., "Positive selection of synonymous mutations in vesicular stomatitis virus", J Mol Biol. 342(5), 2004, 1415-1421.
Rolls, et al., "Expression of additional genes in a vector derived from a minimal RNA virus", Virology 218(2), 1996, 406-411.
Rose, et al., "Hybrid alphavirus-rhabdovirus propagating replicon particles are versatile and potent vaccine vectors", Proc Natl Acad Sci U S A. 105(15), 2008, 5839-5843.
Schell, et al., "Significant protection against high-dose simian immunodeficiency virus challenge conferred by a new prime-boost vaccine regimen", J Virol. 85(12), 2011, 5764-5772.
Extended European Search Report for European Patent Application No. 15793197.3 dated Nov. 20, 2017.
Lundstrom, et al., "Novel Semliki Forest virus vectors with reduced cytotoxicity and temperature sensitivity for long-term enhancement of transgene expression", Mol Ther. 7(2), 2003, 202-209.
Rose, et al. "In vitro evolution of high-titer, virus-like vesicles containing a single structural protein", Proc Natl Acad Sci U S A. 111(47), 2014, 16866-16871.

*Primary Examiner* — Barry A Chestnut
(74) *Attorney, Agent, or Firm* — Saul Ewing Arnstein & Lehr LLP; Kathryn Doyle

(57) ABSTRACT

The present invention relates to the discovery of compositions and methods for therapeutic immunization for treatment of chronic hepatitis B. Methods of the invention include a method generating an evolved high titer hybrid-hepatitis B virus (HBV) vector, methods of treating and/or preventing HBV, and methods of inducing a memory T and B cell immune response against HBV infection in a subject administered the VLV composition produced thereby. Furthermore, the invention encompasses a pharmaceutical composition for vaccinating a subject to protect the subject against infection with HBV.

26 Claims, 11 Drawing Sheets

FIG. 1A

Construction of VLV-HBV vectors

α= antibody

VLV-MHBs immunization is superior to rDNA and rHBsAg
for CD8 T cell induction

VIRUS LIKE VESICLES (VLVS) BASED VACCINES TO PREVENT OR TREAT CHRONIC HEPATITIS B VIRUS (HBV) INFECTION

CROSS-REFERENCE TO RELATED APPLICATIONS

The present application is a 35 U.S.C. § 371 national phase application from, and claims priority to, International Application No. PCT/US2015/030100, filed May 11, 2015, and published under PCT Article 21(2) in English, which claims priority under 35 U.S.C. § 119(e) to U.S. Provisional Application No. 61/994,166, filed May 16, 2014, all of which applications are incorporated herein by reference in their entireties.

STATEMENT REGARDING FEDERALLY SPONSORED RESEARCH OR DEVELOPMENT

This invention was made with government support under grants R37 AI040357 and R01 AI45510, awarded by National Institute of Health. The government has certain rights in the invention.

BACKGROUND OF THE INVENTION

Hepatitis is a general term meaning "inflammation of the liver" and has a number of causes mainly from viral origin. Hepatitis B is the most common serious liver infection in the world. It is caused by the hepatitis B virus (HBV) which is transmitted through blood and bodily fluids. The infection can occur through direct blood-to-blood contact, unprotected sex, use of contaminated needles, and from an infected woman to her newborn during the delivery process.

HBV is a hepatotrophic DNA virus belonging to the Hepadnaviridae family. The virus particle, virion, consists of an outer lipid envelope and an icosahedral nucleocapsid core composed of protein. The nucleocapsid encloses the viral DNA and a DNA polymerase that has reverse transcriptase activity similar to retroviruses (Locarnini S, 2004. Semin. Liver Dis. 24 (Suppl 1): 3-10). The outer envelope contains embedded proteins which are involved in viral binding and entry in susceptible cells. The full-length of the viral genome is about 3.2 kb, and it has four open reading frames (ORFs) including surface antigen (the "S gene"), core antigen (the "C gene"), DNA polymerase (the "P gene") and a gene of undetermined function referred to as the "X gene" (Guo et al., 2009. Hbpd Int 8 (1): 59-64).

Infection with HBV may lead to acute or chronic hepatitis. In general, people who test positive for the hepatitis B virus for more than six months are diagnosed as having a chronic infection which might lead to liver failure, liver cancer or cirrhosis (Wolfram, Virol J. 2013; 10: 239 and Dienstag J L. Hepatitis B virus infection. N Engl J Med. 2008; 359:1486-1500).

The risk of developing a chronic hepatitis B infection is directly related to the age at which one becomes infected with the virus. Infants and young children are at the greatest risk for becoming chronically infected if exposed to the hepatitis B virus. For instance, 90% of exposed infants will develop chronic infections, 30-50% of exposed children will develop chronic infections and 10% of exposed adults will develop chronic infections. Persons with chronic HBV infection have up to a 300 times higher risk of developing hepatocellular carcinoma than persons without chronic HBV infection. Globally HBV causes 60-80% of the world's primary liver cancers. Every year about 1 million people worldwide die from chronic active hepatitis, cirrhosis or HBV-induced liver cancer. As a consequence, HBV ranks second only to tobacco as a known human carcinogen (www.cdc.gov/hepatitis/HBV, and www.mayoclinic.org/diseases-conditions/hepatitis-b/).

Although vaccines against HBV have been widely used for several decades, the HBV prevalence rate in the population still remains high. Current therapies for chronic HBV infection have only limited inhibitory effects on viral RNA and protein expression and typically suppress but do not eliminate the virus. For instance, the commonly used nucleoside reverse-transcriptase inhibitors Entecavir or Tenofovir suppress HBV replication in chronic HBV patients, but the effect is reversible if therapy is stopped. Moreover, despite the promise of therapeutic immunization for treating chronic HBV, the current HBV vaccine is not effective for therapeutic vaccination. Although it elicits a strong neutralizing antibody response that prevents infection, the current vaccine does not induce the CD8+ T cell response needed to eliminate the virus after infection. The current vaccine is also not optimal for widespread prophylactic vaccination in endemic developing regions of the world, as it does not protect all individuals, the antibody response wanes over time, and multiple doses are required for long-lasting immunity. An improved prophylactic vaccine that provides long-term immunity in a single dose, or an effective therapeutic vaccine that cures chronic HBV, would have a substantial impact on the prevention of HBV-associated chronic liver diseases.

For these reasons, there remains a need in the art for an effective HBV vaccine for both prophylactic and therapeutic use. The present invention addresses this need.

SUMMARY OF THE INVENTION

The present invention provides compositions and methods of use of a high titer hybrid-hepatitis B virus (HBV) vector comprising a DNA sequence comprising a promoter sequence operably linked to a DNA sequence encoding Semliki Forest virus (SFV) non-structural protein nucleotide sequences, operably linked to an SFV subgenomic RNA promoter, operably linked to DNA encoding an HBV antigen or fragment thereof, operably linked to a 2A DNA encoding a 2A peptide, which is in turn operably linked to a vesicular stomatitis virus (VSV) G DNA encoding a VSV G protein. The SFV non-structural protein nucleotide sequences of the high titer HBV vector of the invention comprise at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C and the vector of this invention lacks nucleotide sequences which encode SFV structural proteins. Furthermore, when the vector is propagated in cell culture, titers of at least $10^7$ plaque forming units (pfu) per ml of virus like vesicles (VLVs) are obtained.

In another aspect, the present invention provides compositions and methods of use of a high titer hybrid-hepatitis B virus (HBV) vector comprising a DNA sequence comprising a promoter sequence operably linked to a DNA sequence encoding alphavirus non-structural protein nucleotide sequences, operably linked to an alphavirus subgenomic RNA promoter, operably linked to DNA encoding an HBV antigen or fragment thereof, operably linked to a 2A DNA encoding a 2A peptide, which is in turn operably linked to a vesicular stomatitis virus (VSV) G DNA encoding a VSV G protein. The alphavirus non-structural protein nucleotide sequences of the high titer HBV vector of the invention comprise at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C and the vector of this invention lacks nucleotide sequences which encode alphavirus structural proteins. Furthermore, when the vector is propagated in cell culture, titers of at least $10^7$ plaque forming units (pfu) per ml of virus like vesicles (VLVs) are obtained.

The invention also includes a method of immunizing a subject against HBV infection. The method comprises administering to the subject a composition comprising at least $10^7$ pfu/ml of the VLVs produced by the high titer HBV vector of this invention, wherein expression of the HBV antigen induces an immune response in the subject.

In another aspect, the present invention provides a method of treating and/or preventing a disease in a subject. The method comprises administering a therapeutically effective amount of the composition produced by the high titer HBV vector of this invention to a subject in need of such treatment.

The present invention also provides a method of vaccinating a subject, the method comprising administering to the subject a pharmaceutically acceptable amount of the composition produced by the high titer HBV vector of this invention, wherein administration of the composition elicits an immune response in the subject.

In a further aspect, the present invention provides a method of generating a memory T cell immune response to a HBV antigen or fragment thereof in a subject. The method comprises the steps of administering the composition produced by the high titer HBV vector of this invention to a subject in an amount effective to elicit an immune response in the subject and administering a second effective amount of the composition of this invention at a second, subsequent time period, wherein T memory cells directed against the HBV antigen or fragment thereof are generated in the subject.

The present invention further provides a method of generating an adaptive B cell immune response to a HBV antigen or fragment thereof in a subject. The method comprises the steps of administering the composition produced by the high titer HBV vector of this invention to a subject in an amount effective to elicit an immune response in the subject and administering a second effective amount of the composition of this invention at a second, subsequent time period, wherein B memory cells directed against the HBV antigen or fragment thereof are generated in the subject.

In some embodiments, the promoter sequence of high titer HBV vector is a constitutive promoter. In other embodiments, the promoter sequence is the cytomegalovirus immediate early promoter. In some embodiments, titers of at least $5 \times 10^7$ pfu/ml of VLVs are obtained. In other embodiments, titers of at least $1 \times 10^8$ pfu/ml of VLVs are obtained.

In some embodiments, the HBV antigen or fragment thereof is selected from the group consisting of Hepatitis B surface antigen (HBsAg), Hepatitis B core antigen (HBcAg), Hepatitis B e antigen (HBeAg), Hepatitis B viral protein X (HBx), Hepatitis B virus DNA polymerase, and any combination thereof. In other embodiments, the Hepatitis B surface antigen (HBsAg) is the middle hepatitis B surface (MHBs) protein.

In some embodiments, a composition comprising virus like vesicles (VLVs) produced by the high titer HBV vector of this invention. In other embodiments, the HBV antigen or fragment thereof is selected from the group consisting of Hepatitis B surface antigen (HBsAg), Hepatitis B core antigen (HBcAg), Hepatitis B e antigen (HBeAg), Hepatitis B viral protein X (HBx), Hepatitis B virus DNA polymerase, and any combination thereof. In other embodiments, the Hepatitis B surface antigen (HBsAg) is the middle hepatitis B surface (MHBs) protein. In yet other embodiments, the HBV antigen is associated with hepatitis B virus (HBV) infection.

In some embodiments the disease treating and/or preventing by the compositions and methods of this invention is a hepatitis B virus (HBV) infection. In other embodiments, the HBV infection is a chronic infection.

In some embodiments, the composition that elicits an immune response in the subject is a prophylactic vaccine. In other embodiments, the composition is a therapeutic vaccine. In yet other embodiments, the composition is administered in combination with an adjuvant. In further embodiments, the adjuvant is selected from the group consisting of Freund's complete adjuvant, Freund's incomplete adjuvant, Quil A, Detox, ISCOMs and squalene.

In some embodiments, the subject is a mammal. In other embodiments, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

Figure 1A:
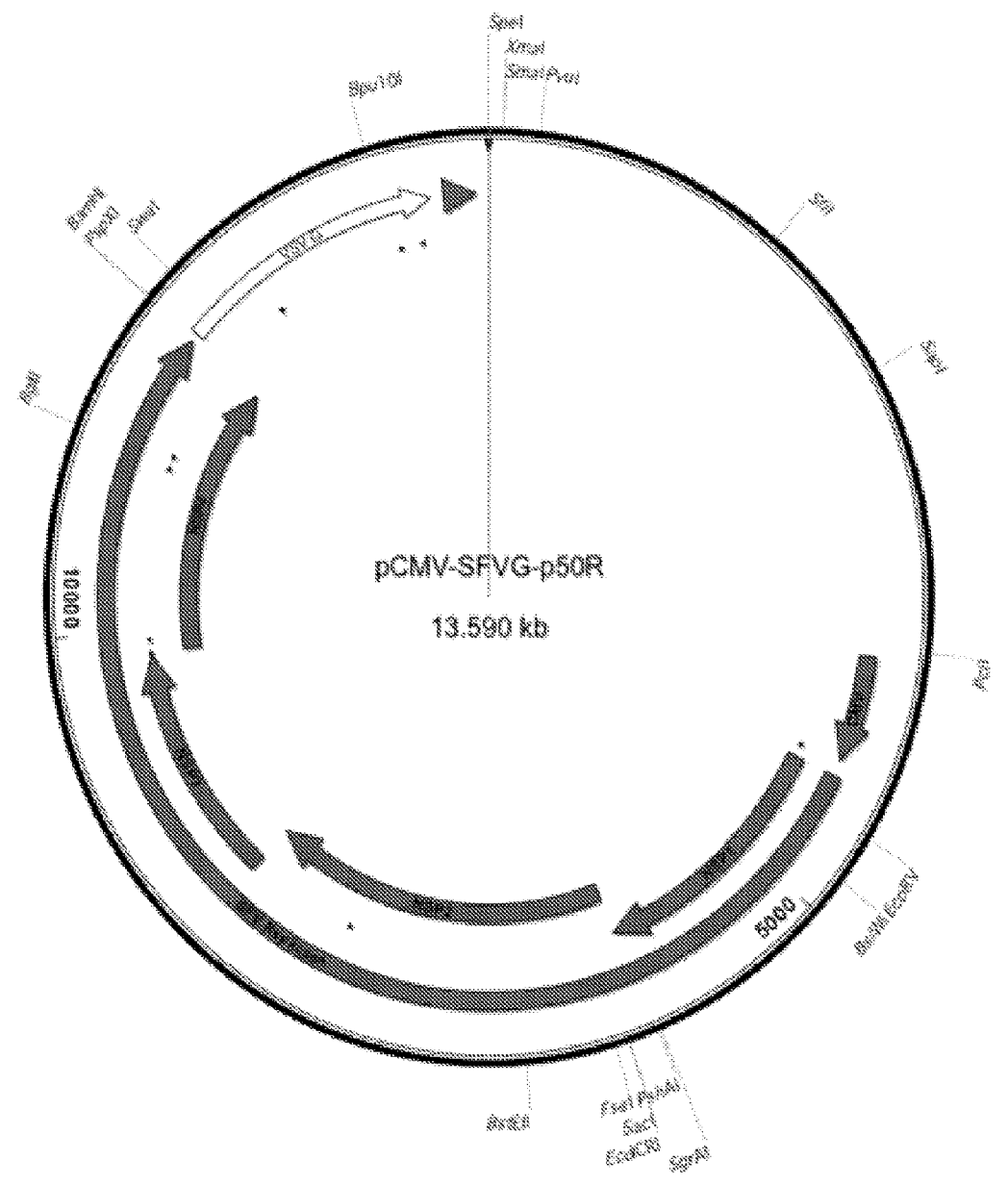

FIGS. 1A-1B are series of diagrams illustrating the VLV DNA construct. FIG. 1A: Map of the p50 RNA genome reconstructed into a DNA vector with the CMV promoter: pCMV-SFVG-p50R. FIG. 1B illustrates a deletion and eleven amino acid changes in high-titer evolved VLVs.

FIG. 2A: Diagram of VLV constructs. FIG. 2B: Western blot of protein expression. FIG. 2C: Immunofluorescence of protein expression.

FIG. 3A: Mice were immunized intramuscularly with $1 \times 10^7$ IFU of VLVs expressing either MHBs or HBcAg. CD8 T cell responses to MHBs or HBcAg were measured by IFN-γ ELISPOT assays at 7 days post immunization, n=10. FIG. 3B: Mice were immunized intramuscularly with $1 \times 10^7$ IFU of VLVs or $1 \times 10^7$ PFU of VSV expressing either MHBs or HBcAg, and circulating antibody responses were determined by ELISA at 30 days post immunization, n=5. *p<0.01.

FIG. 4A: Serum HBeAg levels were determined by ELISA at day 1, 4, and 7 after challenge (n≥4). Percent day 1 levels are shown. FIG. 4B: HBcAg expression in the liver was determined by immunohistochemistry at day 7 post challenge. Quantifications represent average number of HBcAg-positive cells per 100× field (n=3 with 5 fields counted per sample). Representative images are shown. FIG. 4C: At day 7 post challenge, Northern (NB) and Southern blot (SB) analyses were used to determine liver-associated HBV RNA and DNA levels, respectively (n≥3). Representative samples are shown. RC=relaxed circular DNA, SS=single stranded DNA. FIGS. 4D-4E: The T cell recall response was measured at day 7 post challenge by IFN-γ ELISPOT assay in either FIG. 4D splenocytes (n≥4) or FIG. 4E intrahepatic leukocytes (pooled samples from 2 or more mice). Un=Unimmunized.

FIG. 7A: Diagram of $VLV_{NJ}$-MHBs construct. The glycoprotein expressed is derived from the New Jersey serotype VSV. FIGS. 7 B-7C: IFN-γ ELISPOT assays conducted 1 week post boost from mice primed and boosted with the designated MHBs-expressing vaccines. Values are averages of each group (n≥5), error bars represent S. E. VLV=VLV-MHBs, VLVNJ=$VLV_{NJ}$-MHBs, VSV=VSV-MHBs, DNA=pCMV-S2.S.

DETAILED DESCRIPTION OF THE INVENTION

Figure 1B:
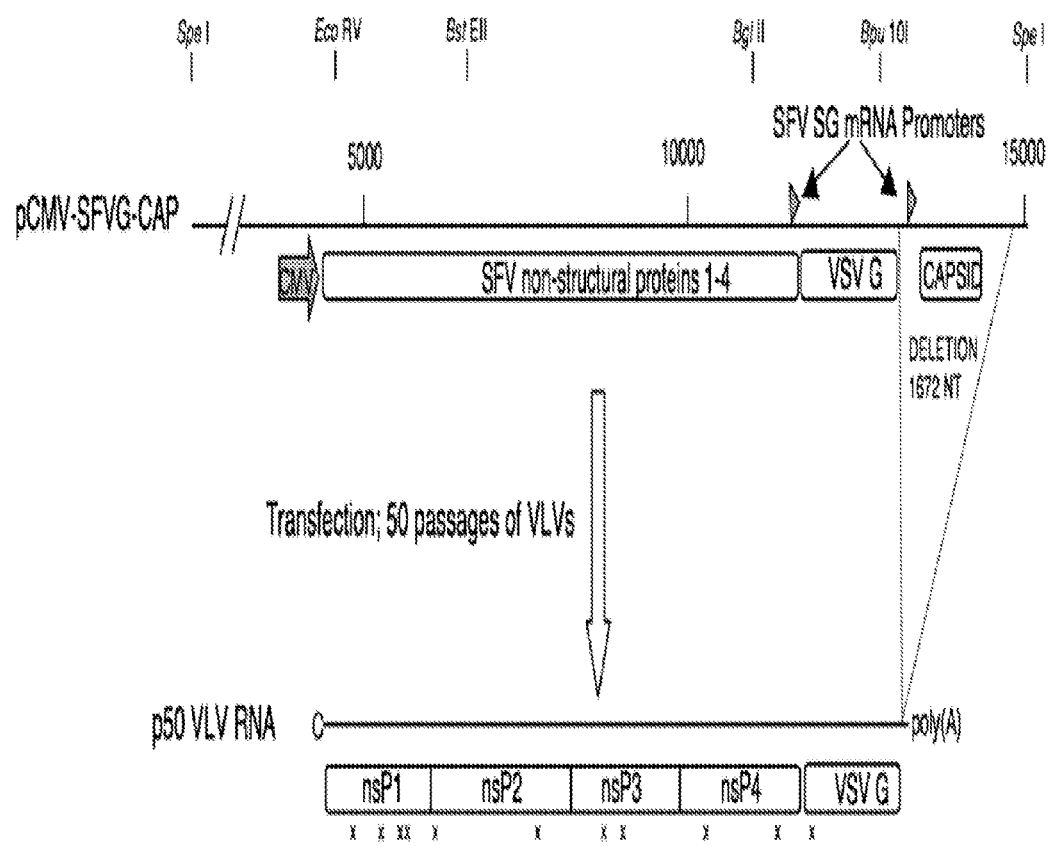

The present invention relates to the discovery of compositions and methods for therapeutic immunization for treatment of chronic hepatitis B. In various embodiments described herein, the methods of the invention include generating an evolved hybrid virus vaccine vector that expresses hepatitis B virus (HBV) structural proteins, wherein the vector produces high titers of virus like vesicles (VLVs). Additionally, the present invention includes methods of treating and/or preventing or immunizing against HBV and methods of generating a memory T and B cell immune response against HBV infection in a subject administered the VLVs of the invention expressing HBV.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, "greater" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween, than a control.

As used herein, the terms "control," or "reference" are used interchangeably, and refer to a value that is used as a standard of comparison.

A "subject" or "patient," as used therein, may be a human or non-human mammal. Non-human mammals include, for example, livestock and pets, such as ovine, bovine, porcine, canine, feline and murine mammals. Preferably, the subject is human.

As used herein, "hepatitis B virus" or "HBV" means hepatitis B virus, including, but not limited to, avian including duck HBV, mammalian including woodchuck and human. The virus is divided into the four major serotypes (adr, adw, ayr, ayw) based on antigenic epitopes presented on its envelope proteins, and the eight genotypes (A-H) defined according to the overall nucleotide sequence variation of the genome. Thus the "HBV" term encompasses geographical genotypes of hepatitis B virus, as well as variant strains of geographical genotypes of hepatitis B virus. Particularly, the human hepatitis B virus may be any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

"Chronic Hepatitis B virus (HBV)" or "Chronic HBV infection", as used herein, includes subjects who have been infected with HBV and who fail to resolve their infection after certain period of time (i.e. 6 months). Persistence of HBsAg for greater than 6 months following an acute infection with HBV is the hallmark of chronic HBV infection. A defective antiviral T cell response has also been documented in human subjects with chronic HBV infection (Boni et al., 1998, J. Clin. Invest., 102 (5): 968-975). These subjects may remain persistently infected with HBV and do not appear to be capable of eliciting a multi-specific polyclonal immune response to several HBV antigens, as compared to those individuals capable of clearing the virus following acute infection. In chronically infected patients exhibiting active infection, the virus replicates in the liver and the disease is mostly mediated by the immune response. "HBV antigen" and "HBV protein" are used herein interchangeably.

As used herein, the term "transfection" includes any means known to the skilled artisan where nucleic sequences are delivered into a cell. Methods of transfecting nucleic acids into cells are described, for example, in Sambrook et al. "Molecular Cloning", A laboratory manual, Cold Spring Harbor Laboratory Press, Volumes 1-3, 2001 (ISBN- 0879695773). Typical transfection methods include electroporation and use of lipids or calcium phosphate.

A "mutation" as used therein is a change in a DNA sequence resulting in an alteration from its natural state. The mutation can comprise deletion and/or insertion and/or duplication and/or substitution of at least one deoxyribonucleic acid base such as a purine (adenine and/or thymine) and/or a pyrimidine (guanine and/or cytosine) Mutations may or may not produce discernible changes in the observable characteristics (phenotype) of an organism (subject).

The term "evolved" or "evolve" as used herein refers to the change (i.e. the evolution) in the inherited characteristics of biological populations over successive generations. Evolutionary processes give rise to diversity at every level of biological organization, including species, individual organisms and molecules such as DNA and proteins (Hall and Hallgrimsson, eds. 2008, Strickberger's Evolution (4th ed.), Jones & Bartlett). In the context of the present invention, the "evolved" hybrid-virus accumulated beneficiary mutations and produced VLVs with 1000 times higher titers after 50 passages in culture than the original hybrid virus.

"Vaccination" refers to the process of inoculating subject with an antigen to elicit an immune response in the subject, that helps to prevent or treat the disease or disorder the antigen is connected with. The term "immunization" is used interchangeably herein with vaccination.

The term "immunogenicity" as used herein, refers to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies that bind to an antigen or organism, a greater diversity of antibodies to an antigen or organism, a greater number of T-cells specific for an antigen or organism, a greater cytotoxic or helper T-cell response to an antigen or organism, a greater expression of cytokines in response to an antigen, and the like.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process The term "activated T cells" indicates T cells that are currently undergoing cell division, cytokine production, performance of regulatory or cytolytic effector functions, and/or has recently undergone the process of "activation."

"Humoral immunity" or "humoral immune response" both refer to B-cell mediated immunity and are mediated by highly specific antibodies, produced and secreted by B-lymphocytes (B-cells).

"Prevention" refers to the use of a pharmaceutical compositions for the vaccination against a disorder.

"Adjuvant" refers to a substance that is capable of potentiating the immunogenicity of an antigen. Adjuvants can be one substance or a mixture of substances and function by acting directly on the immune system or by providing a slow release of an antigen. Examples of adjuvants are aluminium salts, polyanions, bacterial glycopeptides and slow release agents as Freund's incomplete. "Delivery vehicle" refers to a composition that helps to target the antigen to specific cells and to facilitate the effective recognition of an antigen by the immune system. The best-known delivery vehicles are liposomes, virosomes, microparticles including microspheres and nanospheres, polymeres, bacterial ghosts, bacterial polysaccharides, attenuated bacterias, virus like particles, attenuated viruses and ISCOMS.

"Incorporated into" or "encapsulated in" refers to an antigenic peptide that is within a delivery vehicle, such as microparticles, bacterial ghosts, attenuated bacteria, virus like particles, attenuated viruses, ISCOMs, liposomes and preferably virosomes.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid.

"Transform", "transforming", and "transformation" is used herein to refer to a process of introducing an isolated nucleic acid into the interior of an organism.

The term "treatment" as used within the context of the present invention is meant to include therapeutic treatment as well as prophylactic, or suppressive measures for the disease or disorder. As used herein, the term "treatment" and associated terms such as "treat" and "treating" means the reduction of the progression, severity and/or duration of a disease condition or at least one symptom thereof. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

The term "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom. Biological samples may also include sections of tissues such as frozen sections taken for histological purposes.

The term "equivalent," when used in reference to nucleotide sequences, is understood to refer to nucleotide sequences encoding functionally equivalent polypeptides. Equivalent nucleotide sequences will include sequences that differ by one or more nucleotide substitutions, additions- or deletions, such as allelic variants; and will, therefore, include sequences that differ from the nucleotide sequence of the nucleic acids described herein due to the degeneracy of the genetic code.

"Hybridization" refers to any process by which a strand of nucleic acid binds with a complementary strand through base pairing. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. Hybridization also includes the formation of duplexes which contain certain mismatches, provided that the two strands are still forming a double stranded helix. "Stringent hybridization conditions" refers to hybridization conditions resulting in essentially specific hybridization. The term "specific hybridization" of a probe to a target site of a template nucleic acid refers to hybridization of the probe predominantly to the target, such that the hybridization signal can be clearly interpreted. As further described herein, such conditions resulting in specific hybridization vary depending on the length of the region of homology, the GC content of the region, the melting temperature "Tm" of the hybrid. Hybridization conditions will thus vary in the salt content, acidity, and temperature of the hybridization solution and the washes.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. An "isolated cell" or "isolated population of cells" is a cell or population of cells that is not present in its natural environment.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The term "variant," when used in the context of a polynucleotide sequence, may encompass a polynucleotide sequence related to that of a gene or the coding sequence thereof. This definition may also include, for example, "allelic," "splice," "species," or "polymorphic" variants. The polypeptides generally will have significant amino acid identity relative to each other. A polymorphic variant is a variation in the polynucleotide sequence of a particular gene between individuals of a given species. Polymorphic variants may encompass "single nucleotide polymorphisms" (SNPs) in which the polynucleotide sequence varies by one base. The presence of SNPs may be indicative of, for example, a certain population, a disease state, or a propensity for a disease state.

The term "ameliorating" or "treating" means that the clinical signs and/or the symptoms associated with a disease are lessened as a result of the actions performed. The signs or symptoms to be monitored will be well known to the skilled clinician.

As used herein, by "combination therapy" is meant that a first agent is administered in conjunction with another agent. "In conjunction with" or "in combination with" refers to administration of one treatment modality in addition to another treatment modality. As such, "in conjunction with" or "in combination with" refers to administration of one treatment modality before, during, or after delivery of the other treatment modality to the individual. Such combinations are considered to be part of a single treatment regimen or regime.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

"Titers" are numerical measures of the concentration of a virus or viral vector compared to a reference sample, where the concentration is determined either by the activity of the virus, or by measuring the number of viruses in a unit volume of buffer. The titer of viral stocks are determined, e.g., by measuring the infectivity of a solution or solutions (typically serial dilutions) of the viruses, e.g., on HeLa cells using the soft agar method (see, Graham & Van Der eb (1973) Virology 52:456-467) or by monitoring resistance conferred to cells, e.g., G418 resistance encoded by the virus or vector, or by quantitating the viruses by UV spectrophotometry (see, Chardonnet & Dales (1970) Virology 40:462-477).

As used herein, the term "concurrent administration" means that the administration of the first therapy and that of a second therapy in a combination therapy overlap with each other.

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "antibody" or "Ab" as used herein, refers to a protein, or polypeptide sequence derived from an immunoglobulin molecule which specifically binds to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv) and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). An antibody may be derived from natural sources or from recombinant sources. Antibodies are typically tetramers of immunoglobulin molecules.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Heterologous antigens" used herein to refer to an antigen that is not endogenous to the organism comprising or expressing an antigen. As an example, a virus vaccine vector comprising or expressing a viral or tumor antigen comprises a heterologous antigen.

A "fusion protein" as used herein refers to a protein wherein the protein comprises two or more proteins linked together by peptide bonds or other chemical bonds. The proteins can be linked together directly by a peptide or other chemical bond, or with one or more amino acids between the two or more proteins, referred to herein as a spacer.

As defined herein, an "Alphavirus" is a member of the Group IV Togaviridae family of viruses. Alphaviruses include, but are not limited to Aura virus, Babanki virus, Barmah Forest virus, Bebaru virus, Cabassou virus, Chikungunya virus, Eastern equine encephalitis virus, Everglades virus, Fort Morgan virus, Getah virus, Highlands virus, Kyzylagach virus, Mayaro virus, Me Tri virus, Middelburg virus, Mosso das Pedras virus, Mucambo virus, Ndumu virus, O'nyong'nyong virus, Pixuna virus, Rio Negro virus, Ross River virus, Sagiama virus, Salmon pancreas disease virus, Semliki Forest virus, Sindbis virus, Southern elephant seal virus, Tonate virus, Trocara virus, Una virus, Venezuelan equine encephalitis virus, Western equine encephalitis virus and Whataroa virus.

As herein defined, an "alphavirus non-structural protein" can be selected from the group consisting of nsp1, nsp2, nsp3 and nsp4.

As defined herein, an "alphavirus structural protein" can be selected from the group consisting of an alphavirus capsid protein and at least one spike protein.

The term "specifically binds", "selectively binds" or "binding specificity" refers to the ability of the humanized antibodies or binding compounds of the invention to bind to a target epitope present on VSV with a greater affinity than that which results when bound to a non-target epitope. In certain embodiments, specific binding refers to binding to a target with an affinity that is at least 10, 50, 100, 250, 500, or 1000 times greater than the affinity for a non-target epitope.

As used herein, the term "effective amount" or "therapeutically effective amount" means the amount of the virus like vesicle generated from vector of the invention which is required to prevent the particular disease condition, or which reduces the severity of and/or ameliorates the disease condition or at least one symptom thereof or condition associated therewith.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. In the present disclosure, the term "vector" includes an autonomously replicating virus.

The terms "2A" or "2A peptide" or "2A-like peptide" is a self-processing viral peptide. The 2A peptide can separate different protein coding sequences in a single ORF transcription unit (Ryan et al., 1991, J Gen Virol 72:2727-2732). Although termed a "self-cleaving" peptide or protease site, the mechanism by which the 2A sequence generates two proteins from one transcript occurs by ribosome skipping where a normal peptide bond is impaired at 2A, resulting in two discontinuous protein fragments from one translation event. Linking with 2A peptide sequences results in cellular expression of multiple, discrete proteins (in essentially equimolar quantities) derived from a single ORF (de Felipe et al., 2006, Trends Biotechnol 24:68-75).

Description

Compositions

The invention is based in part on the discovery of the high titer hybrid-virus vector illustrated in FIGS. 1A-1B. The vector comprises a DNA sequence comprising a first promoter sequence operably linked to a DNA sequence encoding Semliki Forest virus (SFV) non-structural protein nucleotide sequences comprising at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, A-11560-A, A-11871-G and T-11978-C as shown in Table 2. These sequences are operably linked to DNA specifying a second promoter sequence corresponding to the SFV subgenomic RNA promoter. This sequence is in turn operably linked to DNA encoding a vesicular stomatitis virus (VSV) G protein. The vector lacks functional nucleotide sequences which encode SFV structural proteins. When the vector is propagated in cell culture, high titers of virus like vesicles (VLVs) are obtained, for example, titers of at least $10^7$ plaque forming units (pfu) per ml are obtained.

In some embodiments, the vector of this invention comprises a DNA sequence comprising a first promoter sequence operably linked to a DNA sequence encoding alphavirus non-structural protein nucleotide sequences comprising at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C as shown in Table 2. These sequences are operably linked to DNA specifying a second promoter sequence corresponding to the alphavirus subgenomic RNA promoter. This sequence is in turn operably linked to DNA encoding a vesicular stomatitis virus (VSV) G protein. The vector lacks functional nucleotide sequences which encode SFV structural proteins. When the vector is propagated in cell culture, high titers of virus like vesicles (VLVs) are obtained, for example, titers of at least $10^7$ plaque forming units (pfu) per ml are obtained.

Methods of making the high titer hybrid-virus vector of the invention are described in detail in the Experimental Examples Section herein.

In one aspect, the VSV encoding the VSV G protein can be from any VSV serotype known in the art. Non-limiting examples of VSV serotypes include the Indiana (IND-VSV) serotype and New Jersey (NJ-VSV) serotype.

In one aspect, although the cytomegalovirus immediate early promoter is exemplified herein, the invention should not be construed to be limited to this promoter sequence. Promoter sequences that are useful in the invention include any promoter that induces high levels of gene expression. Such promoters may include, but are not limited to those disclosed elsewhere herein.

In another aspect of the invention, the hybrid-virus vector may achieve titers of at least $5 \times 10^7$ pfu/ml, at least $1 \times 10^8$ pfu/ml or more when the hybrid-virus vector is propagated in cell culture.

In a further aspect of the composition of the invention, DNA encoding a HBV protein is inserted between the subgenomic SFV promoter and DNA encoding the VSV G protein wherein the DNA encoding the heterologous protein is operably linked to DNA encoding a T2A peptide from Thosea asigna virus (Szymczak et al., 2004. Nature Biotechnology 22:589-594) which is in turn operably linked to DNA encoding the VSV G protein. In this way, expression of the HBV protein in the resulting VLVs of the invention is effectively tied to expression of the VSV G protein, the latter being essential for replication of the vector. Thus, expression of the HBV protein is stabilized and the continued presence of the gene expressing this protein in the hybrid vector is assured.

In some embodiments, the 2A peptide is selected from the group consisting of equine rhinitis A virus (E2A), foot-and-mouth disease virus (F2A), porcine teschovirus-1 (P2A), Thosea asigna virus (T2A) and any 2A peptide or fragment thereof known in the art. In further embodiments, the 2A peptide is a T2A peptide or any T2A fragment thereof known in the art.

In certain embodiments, the HBV gene can be under the control of an RNA virus promoter sequence that may not necessarily be the SFV subgenomic promoter sequence. Such modifications and variations of the RNA promoter sequence driving expression of the heterologous promoter sequences will become apparent to those skilled in the art as they practice the invention. The vector may also include conventional control elements which are operably linked to the HBV gene in a manner which permits its transcription, translation and/or expression in a cell infected with the hybrid-virus vector produced by the invention.

In this way, expression of the HBV protein/antigen or fragment thereof is effectively tied to expression of the VSV G protein, the latter being essential for replication of the vector. Thus, expression of the HBV antigen or fragment thereof is stabilized and the continued presence of the gene expressing this protein in the hybrid vector is assured. Such a high titer hybrid-virus vector is referred to herein as a "high titer hybrid-HBV vector."

In certain embodiments, the DNA encoding the HBV antigen or fragment thereof is under the control of a constitutive promoter. In other embodiments, the required component(s) may be under the control of an inducible promoter. Examples of suitable inducible and constitutive promoters are provided elsewhere herein, and are well known in the art.

The vector may also include conventional control elements which are operably linked to the heterologous gene in a manner which permits its transcription, translation and/or expression in a cell infected with the hybrid-virus vector produced by the invention.

As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. There are numerous expression control sequences, including promoters which are native, constitutive, inducible and/or tissue-specific, are known in the art that may be used in the compositions of the invention. "Operably linked" should be construed to include RNA expression and control sequences in addition to DNA expression and control sequences.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, individual elements may function either cooperatively or independently to activate transcription.

In one embodiment, a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. The invention further includes the use of tissue-specific promoter that drive expression of a given heterologous gene in one or more specific types of cells (e.g., desmin promoter, myoglobin promoter, muscle creatine kinase promoter, mammalian troponin 1 promoter, and skeletal alpha-action promoter). Furthermore, any artificial synthetic promoters known in the art can be used in this invention as these promoters can provide optimal efficiency and stability for the heterologous gene. Additionally, enhancer sequences regulates expression of the gene contained within a vector. Typically, enhancers are bound with protein factors to enhance the transcription of a gene. Enhancers may be located upstream or downstream of the gene it regulates. Enhancers may also be tissue-specific to enhance transcription in a specific cell or tissue type.

In order to assess the expression of the DNA encoding the HBV antigen, the expression vector to be introduced into a cell can also contain either a selectable marker gene or a reporter gene or both to facilitate identification and selection of expressing cells from the population of cells sought to be infected through the hybrid-virus vectors. In other aspects, the selectable marker may be carried on a separate piece of DNA and used in a co-infection/transfection procedure. Both selectable markers and reporter genes may be flanked with appropriate regulatory sequences to enable expression in the host cells. Useful selectable markers include, for example, antibiotic-resistance genes, such as the neomycin resistant gene and the like.

Reporter genes are used for identifying potentially infected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

The HBV antigens useful in the high titer hybrid-HBV vector of the invention include Hepatitis B surface antigen (HBsAg), Hepatitis B core antigen (HBcAg), Hepatitis B e antigen (HBeAg), Hepatitis B viral protein X (HBx) and Hepatitis B virus DNA polymerase. In certain aspects, the antigens can be any combination of the HBsAg peptide: the large, middle, and/or small (pre-S1+pre-S2+S, pre-S2+S, or S) In further aspects, the HBV could from any known in the art serotype and genotype as described elsewhere herein. In yet further aspects, the HBV antigen could encompass combinations of HBV antigens (i.e. 2, 3 or more) or a fragment thereof. In some aspects these HBV antigens or HBV antigen's fragments can be assembled into a fusion protein using technology available in the art.

In another aspect of the invention, the hybrid-HBV vector may produce VLVs expressing HBV at titers of at least $5\times10^7$ pfu/ml, at least $1\times10^8$ pfu/ml or more when the VLVs are produced in cell culture.

Methods of the Invention

The invention includes a method of immunizing a subject against infection with HBV. The method comprises administering to the subject a composition comprising virus like vesicles (VLVs) produced by the high titer hybrid virus vector, wherein the high titer hybrid virus vector comprises DNA encoding a HBV gene or fragment thereof. Expression of the heterogeneous gene induces an immune response to the HBV protein or fragment thereof encoded thereby in the subject. In one aspect, the invention includes a method of generating a memory T cell immune response to the HBV protein or fragment thereof in the subject. In another aspect, generating an adaptive B cell immune response the HBV protein or fragment thereof in the subject.

The invention further includes a method of treating a subject in need thereof where the method comprises administering to the subject a composition comprising virus like vesicles (VLVs) produced by the high titer hybrid virus vector of the invention, wherein the high titer hybrid virus vector comprises DNA encoding a HBV gene or fragment thereof and wherein expression of the HBV gene or fragment thereof provides benefit to the subject.

Additionally included in the invention is a method of diminishing the risk that a subject will develop a disease. The method comprises administering to the subject a composition comprising the virus like vesicles (VLVs) produced by the high titer hybrid virus vector of the invention, wherein the high titer hybrid virus vector comprises DNA encoding a HBV gene or fragment thereof. Expression of the HBV gene or fragment thereof induces an immune response to the HBV protein or fragment thereof encoded thereby in the subject, thereby diminishing the risk that the subject will develop HBV.

HBV antigens useful in the methods of the invention include, but are not limited to Hepatitis B surface antigen (HBsAg) or fragment thereof, Hepatitis B core antigen (HBcAg) or fragment thereof, Hepatitis B e antigen (HBeAg) or fragment thereof, Hepatitis B viral protein X (HBx), Hepatitis B virus DNA polymerase or fragment thereof, and any combination of antigens or antigens fragments. In some aspects, combinations of HBV antigens can be assembled into a fusion protein construct.

In certain aspects of the invention, there is a positive correlation between reduction of HBV viral load and antigens, and a decrease of expression, by T cells, of the inhibitory receptor programmed death-1 (PD-1; also known as PDCD1), a negative regulator of activated T cells, upon antiviral therapy and HBeAg seroconversion (Evans et al (2008) Hepatology 48:759).

In another aspect of the present invention contemplates the use of a variant of HBV wherein the variant comprises a nucleotide mutation in the gene encoding at least one of the HBV DNA polymerase, surface antigens, and one/or two open reading frames. The mutation resulting in at least one amino acid addition, substitution and/or deletion of the mutated HBV protein.

In some embodiments, the vaccine generates short and long terms immune responses. Internalization of HBsAg by myeloid dendritic cells inhibits up-regulation of co-stimulatory molecules (i.e. B7) and inhibits T cell stimulatory capacity (den Brouw et al (2008) Immunology 126:280), and dendritic cells from chronically infected patients also show deficits in expression of co-stimulatory molecules, secretion of IL-12, and stimulation of T cells in the presence of HBsAg (Zheng et al., 2004, J. Viral Hepatitis 11:217).

In certain embodiments, the compounds or compositions are designated as a first agent. In certain embodiments, the methods comprise administering a first agent and one or more second agents. In certain embodiments, the methods comprise administering a first agent and one or more second agents. In certain embodiments, the first agent and one or more second agents are co-administered. In certain embodiments the first agent and one or more second agents are co-administered sequentially or concomitantly.

In certain embodiments, the one or more second agents are also a compound or composition described herein. In certain embodiments, the one or more second agents are different from a compound or composition described herein. Examples of one or more second agents include, but are not limited to, an anti-inflammatory agent, chemotherapeutic agent or anti-infection agent.

In other related embodiments, the additional therapeutic agent may be an anti-HBV agent, an anti-HCV agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, or an immunosuppressant agent.

In certain embodiments, the one or more second agents are an anti-HBV agent. In certain embodiments the anti-HBV agent can include, but is not limited to, interferon alpha-2b, interferon alpha-2a, and interferon alphacon-1 (pegylated and unpegylated), ribavirin; an HBV RNA synthesis inhibitor; an HBV capsid assembly inhibitor; a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In certain embodiments, the one or more second agents are an anti-inflammatory agent (i.e., an inflammation lowering therapy). In certain embodiments the inflammation lowering therapy can include, but is not limited to, a therapeutic lifestyle change, a steroid, a NSAID or a DMARD. The steroid can be a corticosteroid. The NSAID can be an aspirin, acetaminophen, ibuprofen, naproxen, COX inhibitors, indomethacin and the like. The DMARD can be a TNF inhibitor, purine synthesis inhibitor, calcineurin inhibitor, pyrimidine synthesis inhibitor, a sulfasalazine, methotrexate and the like.

In certain embodiments, the one or more second agents are a chemotherapeutic agent (i.e., a cancer treating agent). Chemotherapeutic agents can include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin, gemcitabine and diethylstilbestrol (DES).

In certain embodiments, the one or more second agents are an anti-infection agent. Examples of anti-infection agents include, but are not limited to, antibiotics, antifungal drugs and antiviral drugs.

In one embodiment a method for reducing an amount of HBV mRNA, DNA, protein and/or an amount of HBV antigen in a mammal infected with a hepatitis B virus is provided. The method comprises administering to a mammal in need thereof a therapeutically effective amount of a composition comprising the virus like vesicles (VLVs) as described above so as to reduce the hepatitis B virus infection and the hepatitis B antigen, compared to the amount of HBV mRNA, protein and an amount of HBV antigen in the mammal before treatment.

Pharmaceutical Compositions and Formulations.

The high titer hybrid-HBV vector of the invention may be formulated as a pharmaceutical composition.

Such a pharmaceutical composition may be in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between $10^5$ and $10^9$ PFU per immunization. Multiple doses may be administered weekly, monthly, or any combination determined by the skilled artisan.

In one embodiment, the pharmaceutical compositions useful for practicing the method of the invention may comprise an adjuvant. Suitable adjuvants contemplated by this invention include but are not limited to Freund's complete adjuvant, Freund's incomplete adjuvant, Quil A, Detox, ISCOMs or squalene. Pharmaceutical compositions that are useful in the methods of the invention may be suitably developed for inhalation, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human subject being treated, and the like.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans, other primates and mammals including chickens, pigs, squirrels and woodchucks.

The composition of the invention may comprise a preservative from about 0.005% to 2.0% by total weight of the composition. The preservative is used to prevent spoilage in the case of exposure to contaminants in the environment.

Administration/Dosing

The regimen of administration may affect what constitutes an effective amount. For example, the high titer hybrid-virus vector of the invention may be administered to the subject in a single dose, in several divided dosages, as well as staggered dosages may be administered daily or sequentially, or the dose may be continuously infused, or may be a bolus injection. Further, the dosages may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat the disease in the subject. An effective amount of the composition necessary to achieve the intended result will vary and will depend on factors such as the disease to be treated or prevented, the age, sex, weight, condition, general health and prior medical history of the subject being treated, and like factors well-known in the medical arts. In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the composition and the heterologous protein to be expressed, and the particular therapeutic effect to be achieved.

Routes of Administration

One skilled in the art will recognize that although more than one route can be used for administration, a particular route can provide a more immediate and more effective reaction than another route. Routes of administration of any of the compositions\of the invention include inhalation, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Kit

In some embodiments a kit is provided for treating, preventing, or ameliorating an HBV-related disease, disorder or condition, or a symptom thereof, as described herein wherein the kit comprises: a) a compound or compositions as described herein; and optionally b) an additional agent or therapy as described herein. The kit can further include instructions or a label for using the kit to treat, prevent, or ameliorate the HBV-related disease, disorder or condition. In further embodiment, the invention is a kit for assays for variant HBV. Such kits may, for example, contain the reagents from PCR or other nucleic acid hybridization technology (microarrays) or reagents for immunologically based detection techniques (ELISpot, ELISA).

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the experiments disclosed herein are now described.

Materials and Methods

Cell Lines, Hybrid Vesicular Stomatitis Virus/Semliki Forest Virus Vaccine Vector (VLV) Generation.

Hamster BHK-21 (BHK) epithelial cells were maintained in Dulbecco modified Eagle medium (DMEM) supplemented with 10% fetal bovine serum, 50 U/ml penicillin, and 2 mM L-glutamine.

The open reading frames of HBcAg and MHBs were PCR amplified from the pHBV2 plasmid (serotype ayw) introducing upstream Pac1 and downstream Sbf1 sites for directional cloning. Primers used include the following: for HBcAg (core), 5'-GAT CGA TCT TAA TTA AAA TGG ACA TCG ACC CTT ATA AAG ATT TG-3' (forward, SEQ ID NO: 1) and 5'-GAT CGA TCC CTG CAG GAC ATT GAG ATT CCC GAG ATT GAG ATC-3' (reverse, SEQ ID NO: 2) and for MHBs, 5'-GAT CGA TCT TAA TTA AAA TGC AGT GGA ATT CCA CAA CCT TC-3' (forward, SEQ ID NO: 3) and 5'-GAT CGA TCC CTG CAG GAA TGT ATA CCC AAA GAC AAA AGA AAA TTG-3' (reverse, SEQ ID NO: 4). After digestion with the enzymes Pac1 and Sbf1, the PCR products were cloned into plasmid pCMV-SFVT2AG to create pCMV-SFVHBcT2AG and pCMV-SFVmST2AG, respectively. pCMV-SFVT2AG is a plasmid derived from the pCMV-SFVG-p50R vector (SEQ ID NO: 5, provided elsewhere herein at the end of the Examples section.) that has been engineered with a Pac1 to Sbf1 cloning site downstream of the SFV subgenomic RNA promoter. This plasmid also encodes a ribosomal T2A skipping site downstream of the cloning site but upstream of the Indiana serotype VSV glycoprotein (VSV G). A similar plasmid encoding the New Jersey serotype VSV glycoprotein (pCMV-SFVT2AGNJ) was also used for cloning in order to produce virus-like vesicles (VLVs) that express the HBV proteins and the alternate glycoprotein. VLV-MHBs (Indiana serotype), VLV-HBcAg, or VLV$_{NJ}$-MHBs were recovered by transfecting BHK cells with the plasmids pCMV-SFVmST2AG, pCMV-SFVHBcT2AG, or pCMV-SFVmST2AGNJ, respectively. For VLV recovery, BHK-21 cells in 10 cm dishes (2×10$^6$ cells) were transfected with 10 µg of plasmid using Lipofectamine (Invitrogen) and Opti-MEM medium following manufacturers protocol. After 5 hrs, the transfection medium was replaced with 10 mL Dulbecco modified Eagle medium (DMEM) plus 5% FBS. Cells were then incubated at 37° C., 5% CO$_2$ for 48 hrs. Supernatant was then collected. In some cases, VLVs were concentrated by centrifugation through a 100 kDa Amicron® Ultra filter (EMD Millipore Corporation). Aliquots stored at −80° C.

Indirect Immunofluorescence.

Titers of VLV stocks were determined as previously described (Rose et al., 2008, PNAS 105:5839-43). Briefly, stocks were serially diluted and used to infect BHK-21 cells seeded on coverslips for 21 hrs. Cells were then fixed with 3% paraformaldehyde and stained with primary antibodies for the VSV glycoprotein followed by Alexa Fluor 488 goat anti-mouse IgG (H+L) (Invitrogen). Fluorescent plaques of infected cells were then counted and titers were calculated. For immunofluorescence of HBV proteins, cells were transfected with SFVG41-MHBs or SFVG41-HBcAg and fixed with 3% paraformaldehyde and then stained with antibodies for HBV core (Dako), or preS2 (Santa Cruz Biotechnology). Appropriate secondary antibodies were used and cells were imaged using a Nikon Eclipse 80i microscope equipped with a CoolSnap EZ digital camera.

Immunohistochemistry

Liver tissue was collected and fixed in 10% buffered formalin phosphate (Fisher Scientific). After paraffin embedding, HBV core was detected by immunohistochemical staining performed by Yale University Research Histology using anti-core polyclonal rabbit antibody (Dako).

Western Blot.

BHK-21 cells were infected with VLV-MHBs or VLV-HBcAg (MOI of 10) for 24 hrs. Cells were then washed with phosphate-buffered saline (PBS) and lysed with 2× SDS sample buffer. Samples were run on a 10% SDS gel, transferred to a nitrocellulose membrane, probed with either anti-preS2 (Santa Cruz Biotechnology) anti-core (Dako), anti-VSV, or anti-actin (Santa Cruz Biotechnology) antibodies, and then detected with secondary antibody using chemiluminesence.

T Cell Assays.

A gamma interferon (IFN-γ) enzyme-linked immunospot (ELISPOT) set (BD Biosciences) was used to quantify HBV specific T cell responses following the manufacturers protocol. Briefly, at day 7 post-immunization/challenge, mice were euthanized and spleens were collected. Splenocytes were purified by passage through 70-µm strainers (BD Falcon) and treatment with ACK lysing buffer (Lonza). Cells were washed with Hanks' balanced salt solution (HBSS; Invitrogen), suspended in DMEM supplemented with 10% fetal bovine serum, 100 µg/ml penicillin, and 2 mM 1-glutamine and seeded at 2×10$^5$ cells/well in a 96-well plate coated with purified anti-mouse IFN-γ antibody (1:200). The cells were then stimulated overnight at 37° C. with HBV-specific peptides (MHBs and HBcAg, Table 1 below) at a concentration of 10 µg/ml. Cells were washed from plates using PBS-Tween (0.05% [vol/vol]) and the provided biotinylated anti-mouse IFN-γ antibody (1:250) was added for 2 h at 25° C. using DMEM supplemented with 10% fetal bovine serum, 100 µg/ml penicillin, and 2 mM L-glutamine. After washing, streptavidin-horseradish peroxidase (HRP) (1:100) was added to wells and incubated for 1 h at 25° C. Following the final washes, 3-amino-9-ethyl-carbazole (AEC) chromogen-substrate (BD Biosciences) was added to the wells and allowed to develop at 25° C. for 20 to 40 min. Distilled water was added to stop the reaction, and the plates were allowed to air dry before spot-forming cells (SFC) were enumerated.

TABLE 1

| HBV envelope and core CD8 T cell epitopes. | | | | |
|---|---|---|---|---|
| Epitope | Protein | Position | Sequence | MHC |
| 191 | HBV S | 191-202 | IPQSLDSWWTSL | $L^d$ |
| 353 | HBV S | 353-360 | VWLSVIWM | $K^b$ |
| 364 | HBV S | 364-372 | WGPSLYSIL | $D^d$ |

TABLE 1-continued

HBV envelope and core CD8 T cell epitopes.

| Epitope | Protein | Position | Sequence | MHC |
|---|---|---|---|---|
| 371 | HMV S | 371-378 | ILSPFLPL | $K^b$ |
| 87 | HBcAg | 87-95 | SYVNTNMGL | $K^d$ |
| 93 | HBcAg | 93-100 | MGLKFRQL | $K^b$ |
| 131 | HBcAg | 131-139 | AYRPPNAPI | $K^d$ |

Mice

Six to eight-week old C57BL/6×Balb/c F1 (CB6F1J) mice were obtained from Jackson Labs (Farmington, Conn.). For transgenic (Tg) mouse experiments, 1.3.32 HBV Tg mice (15) and Balb/c mice (Charles River; Wilmington, Mass.) were crossed for one generation to obtain HBV.CB6F1 mice. Mice were screened at 5-6 weeks for serum HBeAg levels as a measure of transgene expression.

Immunization and Challenge Protocols

Mice were immunized intramuscularly with $10^7$ immunofluorescence units (IFU) of VLV-MHBs or VLV-HBcAg, $10^7$ PFU of VSV-MHBs, or 50 µg of pCMV-S2.S. In some cases, mice were boosted 4 weeks post immunization with either $10^7$ PFU of VSV-MHBs, VLV-MHBs or $VLV_{NJ}$-MHBs.

For challenge studies, immunized mice were kept for 6 weeks and then challenged using a hydrodynamic transfection protocol, which involves injection of 10 µg of pHBV1.3 into the mouse's tail vein in a volume of PBS equal to 9% of its body weight (Yang et al., 2002). Serum was collected and days 1, 4, and 7 post-challenge and used to monitor HBeAg levels by HBeAg ELISA (International Immuno-Diagnostics).

ELISAs

In order to detect antibody responses to MHBs and HBcAg and serum HBeAg levels, enzyme-linked immunosorbant assays (ELISAs, International Immunodiagnostics) were performed following the manufacturers protocol, diluting serum samples 1:50 in FBS.

Isolation of Intrahepatic Leukocytes

Intrahepatic leukocytes were isolated as described previously (Cobleigh et al., 2010, Journal of virology 84:7513-7522). Briefly, liver pieces were passed through a 70 µm-pore strainer, and the resulting suspension was treated for 30 min at 37° C. with 0.5 mg/mL collagenase D (Roche). Cells were then washed with HBSS, resuspended in 44% Percoll in HBSS (vol/vol), and layered over 56% Percoll in PBS (vol/vol). After centrifuging the gradient for 30 min at 850×g, the cells at the interphase were collected. The cells were then washed with HBSS and resuspended in DMEM for further analysis.

HBV RNA and DNA Analysis.

After challenge, HBV RNA and DNA were detected by Northern and Southern blot analyses. Total genomic DNA from the liver was purified as described previously (Guidotti et al., 1995). Southern blot analysis was then performed by digesting 30 µg of total liver DNA with HindIII and separating it on an agarose gel. For Northern blot analysis, total liver RNA was isolated using an RNeasy minikit (Qiagen) according to the manufacturer's protocol. Denatured RNA (20 µg) was separated by agarose (containing 5% formaldehyde) gel electrophoresis. Using the capillary transfer method with 10×SSC (0.15 M NaCl with 0.015 M sodium citrate) nucleic acids were transferred to nylon membranes overnight. The nucleic acids were then cross-linked to the membrane by UV irradiation and hybridized to probes prepared from 3.2-kb HBV DNA with 32P-labeled dCTP and a Roche random-primed DNA labeling kit. Signal was detected using a PhosphorImager (Fuji).

Statistical Data Analysis

Student's t-test was used to determine significant differences in CD8 T cell responses in normal and transgenic mice. P values of <0.05 were considered statistically significant.

Nucleotides Sequences for MHBS and HBcAg DNA are Listed Below:

MHBs (5'-3')

(SEQ ID NO: 6)

TTAATTAAAATGCAGTGGAATTCCACAACCTTCCACCAAACTCTGCAAGA

TCCCAGAGTGAGAGGCCTGTATTTCCCTGCTGGTGGCTCCAGTTCAGGAA

CAGTAAACCCTGTTCTGACTACTGCCTCTCCCTTATCGTCAATCTTCTCG

AGGATTGGGGACCCTGCGCTGAACATGGAGAACATCACATCAGGATTCCT

AGGACCCCTTCTCGTGTTACAGGCGGGGTTTTTCTTGTTGACAAGAATCC

TCACAATACCGCAGAGTCTAGACTCGTGGTGGACTTCTCTCAATTTTCTA

GGGGGAACTACCGTGTGTCTTGGCCAAAATTCGCAGTCCCCAACCTCCAA

TCACTCACCAACCTCTTGTCCTCCAACTTGTCCTGGTTATCGCTGGATGT

GTCTGCGGCGTTTTATCATCTTCCTCTTCATCCTGCTGCTATGCCTCATC

TTCTTGTTGGTTCTTCTGGACTATCAAGGTATGTTGCCCGTTTGTCCTCT

AATTCCAGGATCCTCAACAACCAGCACGGGACCATGCCGGACCTGCATGA

CTACTGCTCAAGGAACCTCTATGTATCCCTCCTGTTGCTGTACCAAACCT

TCGGACGGAAATTGCACCTGTATTCCCATCCCATCATCCTGGGCTTTCGG

AAAATTCCTATGGGAGTGGGCCTCAGCCCGTTTCTCCTGGCTCAGTTTAC

TAGTGCCATTTGTTCAGTGGTTCGTAGGGCTTTCCCCCACTGTTTGGCTT

TCAGTTATATGGATGATGTGGTATTGGGGGCCAAGTCTGTACAGCATCTT

GAGTCCCTTTTTACCGCTGTTACCAATTTTCTTTTGTCTTTGGGTATACA

TTCCTGCAGGAG

Gray = restriction sites

HBcAg (5'-3')

(SEQ ID NO: 7)

TTAATTAAAATGGACATCGACCCTTATAAAGAATTTGGAGCTACTGTGGA

GTTACTCTCGTTTTTGCCTTCTGACTTCTTTCCTTCAGTACGAGATCTTC

TAGATACCGCCTCAGCTCTGTATCGGGAAGCCTTAGAGTCTCCTGAGCAT

TGTTCACCTCACCATACTGCACTCAGGCAAGCAATTCTTTGCTGGGGGA

ACTAATGACTCTAGCTACCTGGGTGGGTGTTAATTTGGAAGATCCAGCGT

CTAGAGACCTAGTAGTCAGTTATGTCAACACTAATATGGGCCTAAAGTTC

AGGCAACTCTTGTGGTTTCACATTTCTTGTCTCACTTTTGGAAGAGAAAC

AGTTATAGAGTATTTGGTGTCTTTCGGAGTGTGGATTCGCACTCCTCCAG

CTTATAGACCACCAAATGCCCCTATCCTATCAACACTTCCGGAGACTACT

GTTGTTAGACGACGAGGCAGGTCCCCTAGAAGAAGAACTCCCTCGCCTCG

-continued
CAGACGAAGGTCTCAATCGCCGCGTCGCAGAAGATCTCAATCTCGGGAAT

CTCAATGTCCTGCAGGAG

Gray = restriction sites

Amino Acid Sequences for MHBS and HBcAg Proteins are Listed Below:

MHBs
(SEQ ID NO: 8)
MQWNSTTFHQTLQDPRVRGLYFPAGGSSSGTVNPVLTTASPLSSIFSRIG

DPALNMENITSGFLGPLLVLQAGFFLLTRILTIPQSLDSWWTSLNFLGGT

TVCLGQNSQSPTSNHSPTSCPPTCPGYRWMCLRRFIIFLFILLLCLIFLL

VLLDYQGMLPVCPLIPGSSTTSTGPCRTCMTTAQGTSMYPSCCCTKPSDG

NCTCIPIPSSWAFGKFLWEWASARFSWLSLLVPFVQWFVGLSPTVWLSVI

WMMWYWGPSLYSILSPFLPLLPIFFCLWVYI

HBcAg
(SEQ ID NO: 9)
MDIDPYKEFGATVELLSFLPSDFFPSVRDLLDTASALYREALESPEHCSP

HHTALRQAILCWGELMTLATWVGVNLEDPASRDLVVSYVNTNMGLKFRQL

LWFHISCLTFGRETVIEYLVSFGVWIRTPPAYRPPNAPILSTLPETTVVR

RRGRSPRRRTPSPRRRRSQSPRRRRSQSRESQC

The results of the experiments are now described in the following examples.

Example 1: Extensive Passaging Generates High-Titer VLVs

Figure 2A:
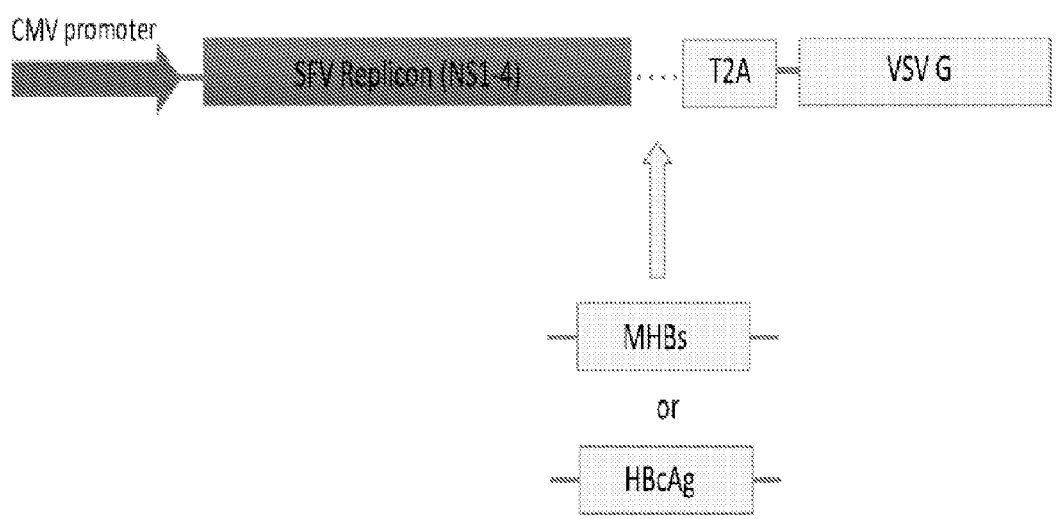
FIGS. 2A-2C are series of diagrams and images depicting the expression of the surface antigens: middle hepatitis B surface (MHBs) protein and the core antigen hepatitis B antigen (HBcAg) protein from VLVs.

To generate VLVs that grow to high titers following evolution though extensive passaging in tissue culture, the starting DNA construct diagramed in FIGS. 1A-1B was used. The SFV replicon generated using this construct expresses VSV G from the first subgenomic promoter and the SFV capsid protein from the second promoter. Infectious particles from this construct were derived and found to exhibit low titers typical of VLVs (~$10^5$ infectious units/ml). Passaging of the VLVs on BHK cells was pursued over a period of one year to determine if it was possible to evolve particles that would grow to higher titers. In the initial passages 5% of the medium from cells showing cytopathic effect (CPE) were transferred onto fresh BHK cells on 6 cm dishes, and strong CPE then developed by 3-5 days. Expression of the SFV capsid protein was completely lost by passage eight suggesting that its expression was inhibiting particle production. With continued passaging an increasing particle titers and a much more rapid CPE developing in less than 24 hours were noticed. By passage fifty the VLVs had evolved to reach titers >$5\times10^7$ i.u./ml and they formed visible plaques of variable sizes on BHK cells after two days. At this point a large plaque was chosen and used to generate a cloned VLV stock which will be referred to subsequently as "p50 VLV". This p50 VLV grows to titers of approximately $5\times10^8$ pfu/ml, an increase of approximately 1000-fold over the starting vector.

Example 2: Sequence of the p50 VLV Genome

To determine a consensus sequence of the p50 VLV genome reverse transcription and PCR were performed to generate overlapping DNA fragments covering the entire genome, and then these fragments were sequenced. The assembled sequence showed a large deletion of 1672 nucleotides (in vector deletion located between nucleotides 13333 and 13334) which had removed the second SFV promoter, the entire capsid gene, and all except 187 nucleotides of SFV sequences preceding the poly(A) (FIGS. 1A-1B).

In addition to this deletion, there were 16 single base changes listed in Table 2 below. Ten of these changed amino acids in all four of the SFV non-structural proteins, one changed an amino acid in VSV G, and four mutations were silent (FIGS. 1A-1B, Table 2).

TABLE 2

Nucleotide and amino acid changes in p50VLVs

| Nucleotide change | Amino acid change and context* | Protein affected |
|---|---|---|
| G-4700-A | G-106-E (AASEKVL) | nsP1 |
| A-5424-G | None | |
| G-5434A | V-351-I (ATDITPE) | nsP1 |
| T-5825-C | L-481-S (KRESIPV) | nsP1 |
| T-5930-C | I-516-T (LVPTAPA) | nsP1 |
| A-6047-G | D-555-G (QPNGVLL) | nsP2 |
| G-6783-A | None | |
| G-6963-A | None | |
| G-7834-A | A-1151-T (ALVTEYK) | nsP2 |
| T-8859-A | None | |
| T-8864-C | M-1494-T (AIDTRTA) | nsP3 |
| G-9211-A | A-1610-T (ERITRLR) | nsP3 |
| A-10427-G | N-2015-S (TLQSVLA) | nsP4 |
| G-11560-A | E-2393-K (SRYKVEG) | nsP4 |
| A-11871-G | N-34-D (NWHDDLI) | VSV G |
| T-11978-C | None | |

*Amino acids are numbered in the SFV nsP1-4 polyprotein, or in the VSV G protein. Bold underlined text indicates the amino acid that was changed.

The nucleotide sequence of the high titer hybrid-virus vector: pCMV-SFVG-p50R (referred as SEQ ID NO: 5) is provided elsewhere herein (at the end of the Examples section).

Example 3: VLV Construction and Expression

The open reading frame of the HBV (ayw serotype) core antigen (HBcAg) and the middle version of the HBV envelope protein (MHBs) were amplified using PCR, adding on cloning sites for Pac1 and Sbf1 on the 5' and 3' ends, respectively. The genes were then cloned into the plasmid pCMV-SFVT2AG to create pCMV-SFVHBcT2AG and pCMV-SFVmST2AG, respectively. pCMV-SFVT2AG is a plasmid derived from pCMV-SFVG-P50R that has been engineered with a Pac1 to Sbf1 cloning site downstream of the SFV subgenomic RNA promoter. This plasmid also encodes a ribosomal T2A skipping site (Doronina et al., 2008, Molecular and cellular biology 28:4227-4239) downstream of the cloning site but upstream of the Indiana serotype VSV glycoprotein (VSV G) (FIG. 2A). A similar plasmid encoding the New Jersey serotype VSV glycoprotein (pCMV-SFVT2AGNJ) was also used for cloning in order to produce virus-like vesicles (VLVs) that express the HBV proteins and the alternate glycoprotein.

Figure 2B:
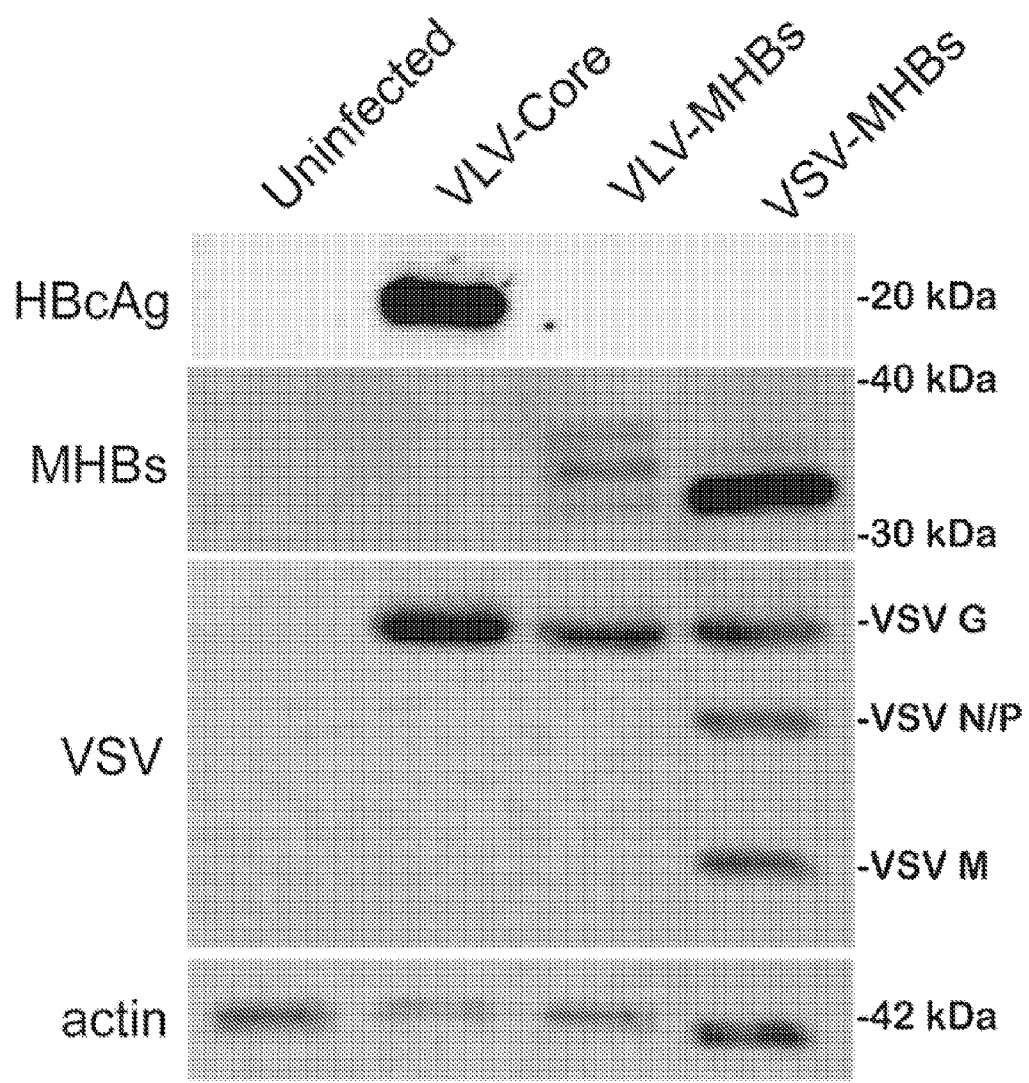
Figure 2C:
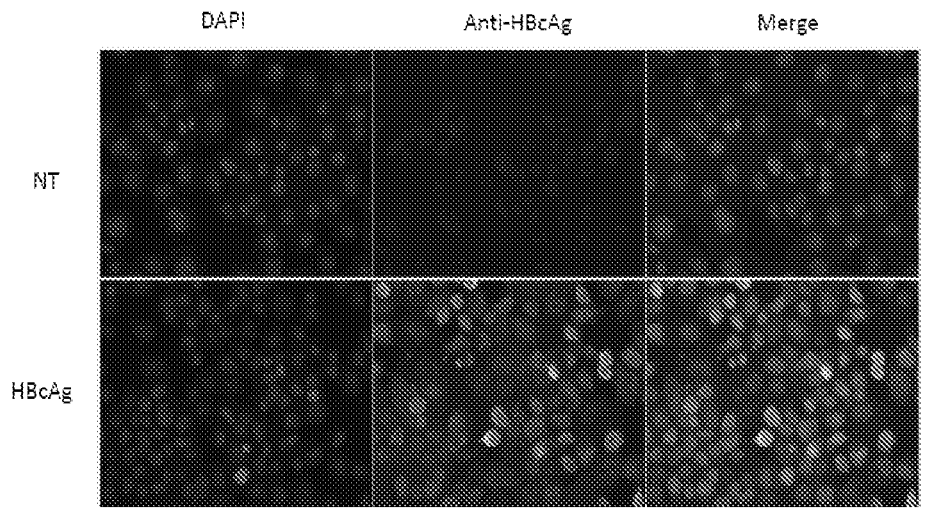
Figure 2C:
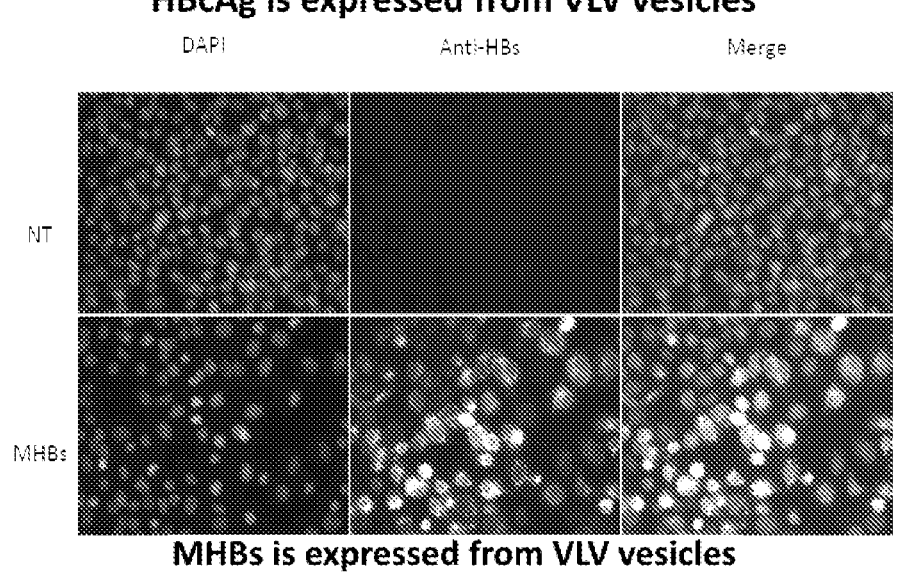
Figures 3A, 3B:
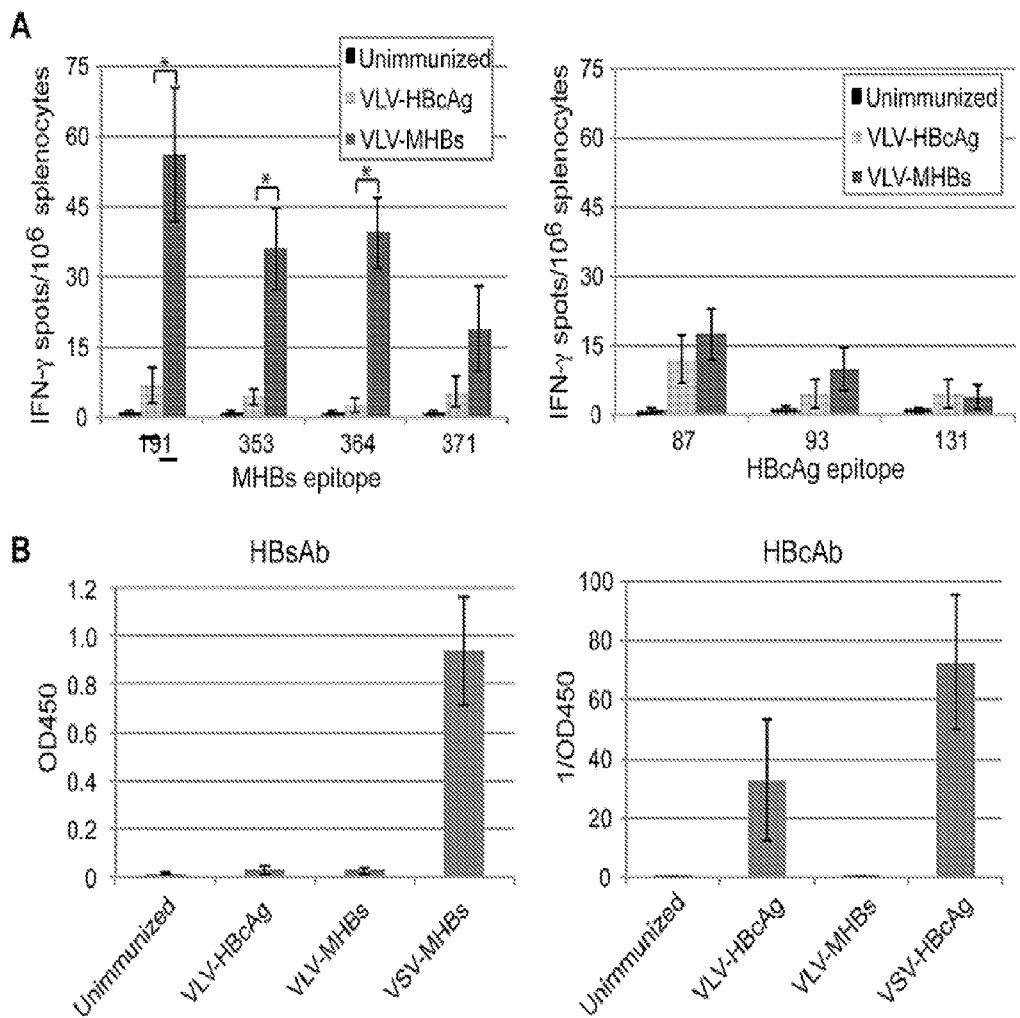
FIGS. 3A-3B are a series of histograms showing that VLVs expressing HBV proteins induce HBV-specific immune responses.
Figure 4A:
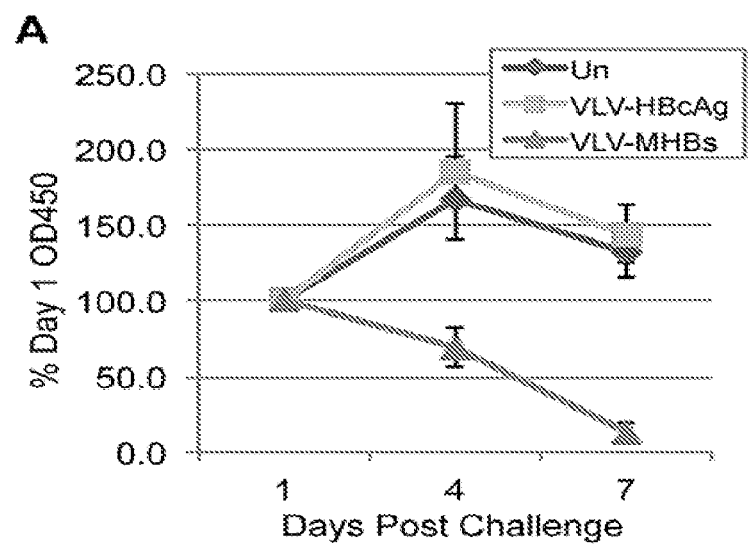
FIGS. 4A-4E are series of graphs and images demonstrating that VLV-MHBs immunized mice are protected from HBV hydrodynamic challenge. Mice were immunized with $10^7$ IFU of VLV-HBcAg or VLV-MHBs, or $10^7$ PFU of VSV-MHBs or VSV-HBcAg. HBV replication was then induced by hydrodynamic injection of HBV 1.3 plasmid (10 μg) at 6 weeks post immunization.
Figure 4B:
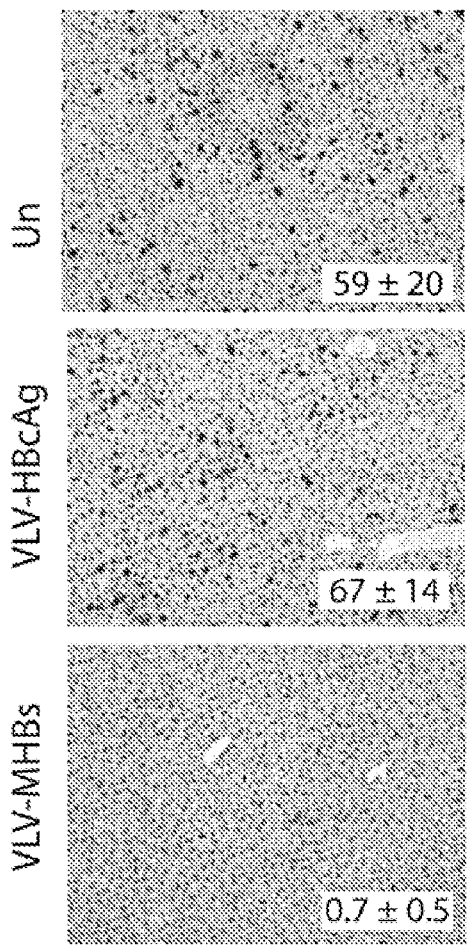
Figures 4C, 4D, 4E:
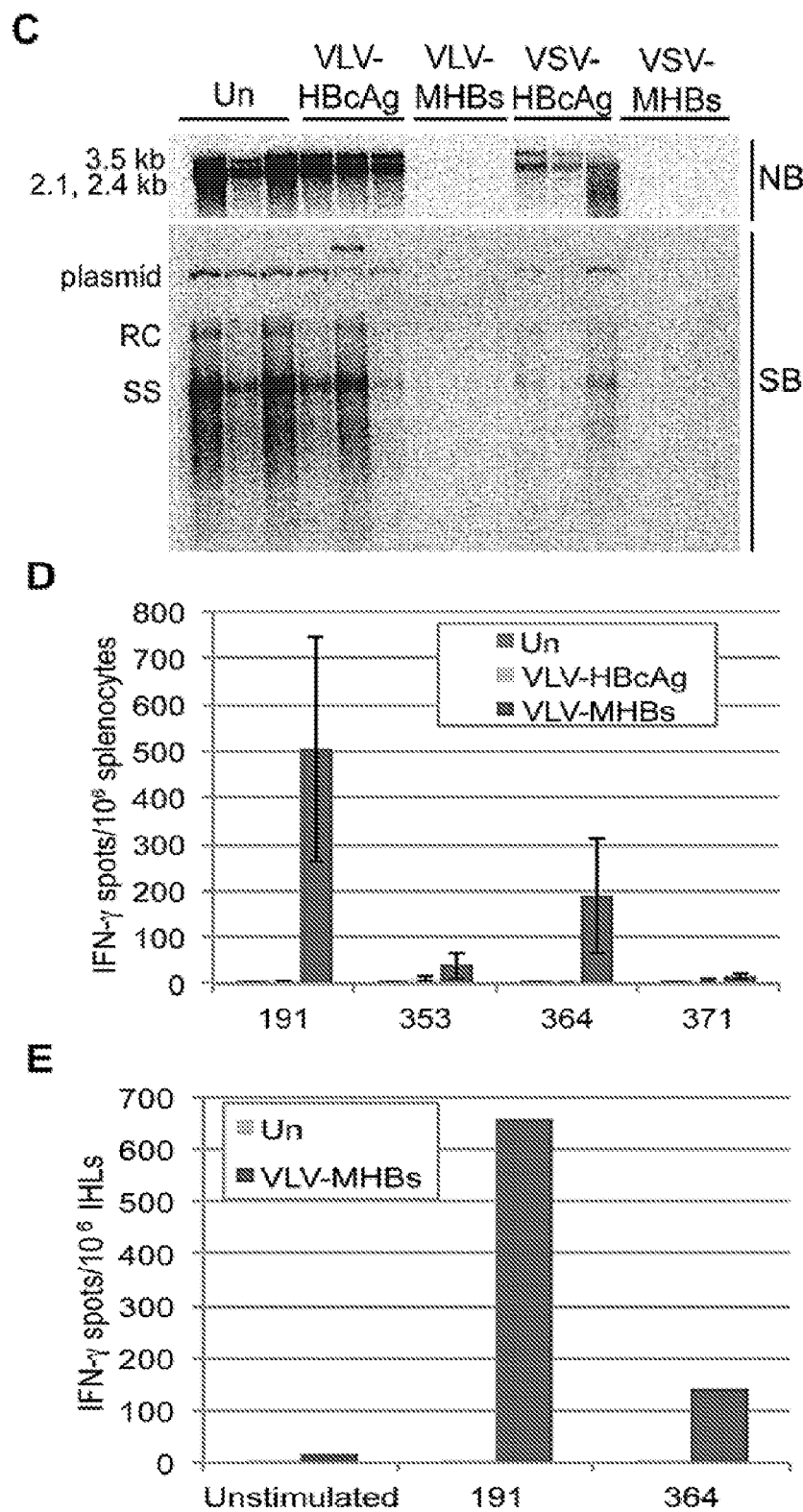
Figure 5:
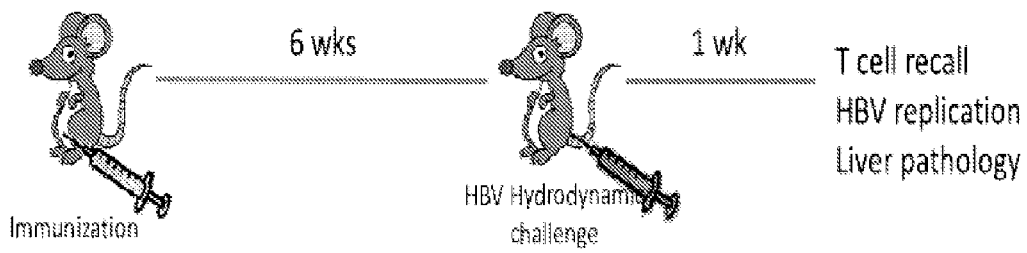
FIG. 5 an image showing a schematic illustration of the immunization protocol.

After cloning into the VLV vector backbone, the VLVs were recovered, and expression of the HBV proteins was determined. After an initial transfection of the VLV plasmid, indirect immunofluorescence was performed to determine if the proteins were expressed. Indeed, transfection of the VLV plasmids leads to expression of MHBs or HBcAg (FIG. 2C). Next, it was determined if the recovered VLVs could express the HBV proteins after infection. Consistent with the transfection data, both HBcAg and the multiple glycosylated forms of MHBs (FIG. 2B) were readily detected. Additionally, strong expression of the VSV glycoprotein after infection with the generated VLVs was also observed (FIG. 1C). The VLVs were typically recovered at titers above $10^8$ IFU/mL.

Example 4: Generation of Vector and Immunization

Figure 6:
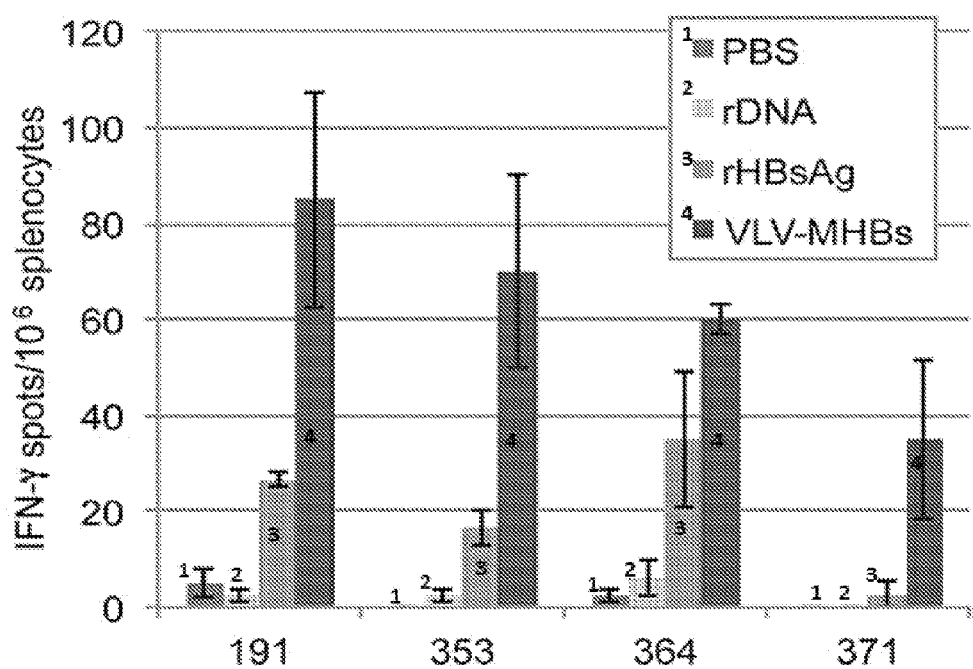
FIG. 6 is a histogram depicting that VLV-MHBs induces superior CD8 T cell responses compared to DNA or protein. Mice were intramuscularly immunized with 50 μg recombinant DNA expressing HBs (pCMV-S2.S), 10 μg recombinant HBsAg, or $10^7$ IFU of VLV-MHBs, and CD8 T cell responses were determined 7 days post immunization by IFN-γ ELISPOT assay (n≥4).

VLV vectors were generated expressing either the middle hepatitis B surface (MHBs) protein (VLV-MHBs) or the core antigen hepatitis B antigen (HBcAg) protein (FIG. 2). The ability of these vectors to induce HBV antigen-specific CD8 T cell responses was examined in mice. Animals were immunized intramuscularly with $1\times10^7$ plaque-forming units (PFU) of VLV-MHBs or VLV-HBcAg, and CD8 T cell responses were measured 7 days later by IFN-γ ELISpot assay using peptides corresponding to known MHBs or HBcAg CD8 T cell epitopes (FIG. 3A). CD8 T cell responses were specifically elicited to four MHBs epitopes in VLV-MHBs-immunized mice (FIG. 3A). In contrast, no responses measurable by this assay were generated to HBcAg in VLV-HBcAg-immunized mice.

Although it is unclear if antibody responses to HBV would be necessary for an effective therapeutic vaccine, anti-HBV responses could potentially play a role in neutralizing free virus and therefore preventing infection or reinfection of host hepatocytes. To determine if the VLV vaccines were able to elicit HBV-specific antibody responses, mice were immunized as described above. Thirty days post immunization, serum HBs or HBcAb levels were examined by ELISA. In contrast to the T cell responses, VLV-MHBs immunization did not elicit detectable HBsAb responses (FIG. 3B). In contrast, immunization with VLV-HBcAg did elicit antibodies specific for HBcAg, though these responses were not as high as a VSV vector expressing HBcAg (VSV-HBcAg; FIG. 3B). Taken together, these data indicate that the VLV vaccine platform is capable of expressing HBV proteins that can elicit an HBV-specific immune response.

Example 5: CD8 T Cells Elicited by VLV-MHBs are Protective in a Model of Acute HBV Infection To determine if the CD8 T cells induced by VLV-MHBs would be protective, an HBV hydrodynamic injection protocol (Yang et al., 2002, PNAS 99:13825-13830) which models an acute HBV infection, was used. This model involves injection of an HBV 1.3 genome length DNA expression plasmid into the tail vein of the mouse in a volume approximately equal to 9% of the mouse's body weight. This volumetric overload forces uptake of the DNA by the mouse's hepatocytes and thus results in expression of HBV proteins and replication intermediates. Because there is no viral entry step in this protocol, protection is dependent on T cell-mediated mechanisms to clear HBV infection. Mice were immunized with DMEM, $10^7$ IFU of VLV-MHBs or VLV-HBcAg, or $10^7$ PFU of VSV-MHBs or VSV-HBcAg. Six weeks post immunization, the hydrodynamic injection was performed, and the mice were monitored for HBV replication.

To examine HBV protein expression after challenge, HBeAg expression in the serum and HBcAg expression in the liver were examined. In all mice, serum HBeAg levels significantly increased by day 1 post challenge. In mice left unimmunized or immunized with VLV-HBcAg, HBeAg continues to increase at day 4 and then levels off at day 7 post challenge. However, in mice immunized with VLV-MHBs, serum HBeAg decreases at day 4 and becomes almost undetectable by day 7 post challenge (FIG. 4A). HBcAg levels in the liver were determined at day 7 post challenge by immunohistochemistry. Consistent with the detected HBeAg levels, the number of HBcAg-expressing hepatocytes was significantly reduced in mice immunized with VLV-MHBs when compared to unimmunized or VLV-HBcAg immunized mice (FIG. 4B).

Next, levels of HBV RNA and DNA in the liver were examined by Northern and Southern blot, respectively. These analyses demonstrated that VLV-MHBs completely protected mice from HBV replication (FIG. 4C). Interestingly, the level of protection demonstrated by VLV-MHBs immunization was similar to that observed for VSV-MHBs, a vector that induces very strong HBV-specific immune responses. In agreement with their inability to induce T cell responses, the VLV- and VSV-HBcAg vectors did not protect mice from challenge (FIG. 4C).

Finally, since CD8 T cells are likely responsible for clearance in this model, the T cell recall response was measured by performing IFN-γ ELISPOT assays 7 days post challenge on both splenocytes (FIG. 4D) and intrahepatic leukocytes (FIG. 4E). The results demonstrate a strong CD8 T cell response to at least 2 of the 4 epitopes tested. Importantly, these responses are approximately 5-fold greater than the response induced after primary immunization (compare FIG. 4D to FIG. 3A). These results suggest that VLV-MHBs particles induce memory T cells that can be recalled and expanded during HBV challenge. Furthermore, these results demonstrate that the T cells induced by VLV-MHBs are capable of controlling HBV infection in this model in the absence of detectable antibody.

Example 7: CD8 T Cells Mediate Response to Four MHBs Epitopes after Immunization with VLV-MHBs, VLV-rDNA, or VLV-rHBsAg CD8 T cell response was compared between MHBs in mice immunized with VLV-MHBs to mice immunized with recombinant DNA (rDNA) expressing MHBs or recombinant HBsAg protein (rHBsAg) (FIG. 6). Mice were immunized intramuscularly with $1\times10^7$ PFU of VLV-MHBs, 50 μg of rDNA, or 10 μg of rHBsAg, and CD8 T cell responses to the four MHBs epitopes were measured seven days later. Mice immunized with control PBS or rDNA did not elicit measurable responses. Although a subset of mice responded to HBsAg protein immunization, the CD8 T cell responses induced by VLV-MHBs immunization were generally greater in magnitude and broader in specificity. Therefore, compared to rDNA or rHBsAg, the CD8 T cell responses generated by VLV-MHBs in mice were more consistently detectable and generally stronger. Furthermore, in mice where responses were detected, the responses were directed towards more epitopes in mice immunized with VLV-MHBs (FIG. 6). These data indicate that VLV-MHBs immunization elicits better CD8 T cell responses than other tested immunization strategies.

Figure 7A:
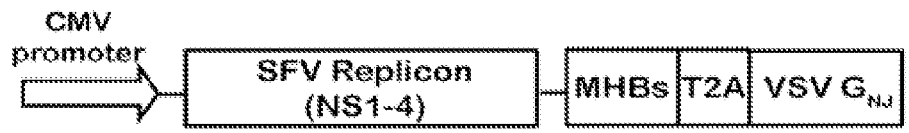
FIGS. 7A-7C are series diagrams and histograms demonstrating that Prime-boost protocols, using VLVs, improve HBV-specific CD8 T cell responses.
Figure 7B:
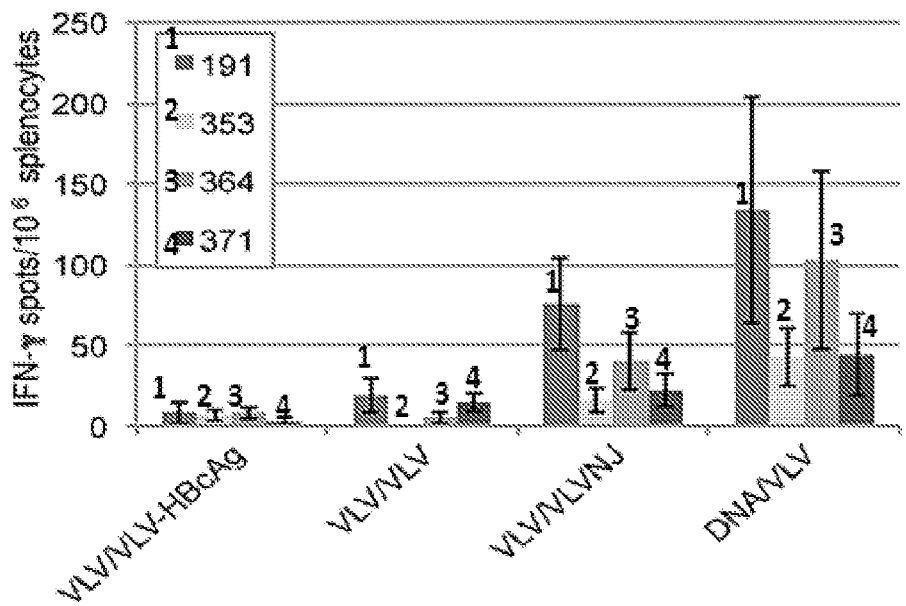

Example 8: Combining Immunization Strategies in a Prime-Boost Protocol Improves HBV-Specific Immune Responses Although VLV-MHBs particles elicit protective T cell responses in a single dose, overcoming immunotolerance during chronic infection may require multiple immunizations. Importantly, antibodies to the VSV G protein would likely neutralize a VLV boosting vector of the same serotype. Therefore, in order to investigate prime-boost strategies using the VLV vaccine platform, an additional VLV construct was first generated. This construct also expresses MHBs, but the VSV G protein (Indiana serotype) was replaced with the New Jersey serotype VSV G ($VLV_{NJ}$-MHBs; FIG. 7A). After constructing $VLV_{NJ}$-MHBs, a prime-boost experiment was performed, intramuscularly priming with VLV-MHBs or 50 μg of a DNA plasmid expressing MHBs (pCMV-S2.S). Then, mice were boosted 4 weeks later with VLV-HBcAg, VLV-MHBs, or $VLV_{NJ}$-MHBs. Seven days post boost, CD8 T cell responses were analyzed by performing IFN-γ ELISPOT assays. Boosting with VLV-HBcAg or VLV-MHBs did not induce a measurable response, as expected (FIG. 7B). Boosting with $VLV_{NJ}$-MHBs did yield a measurable HBV-specific response; however the response observed was no greater than the primary response observed with VLV-MHBs immunization, suggesting that the boost was ineffective. Priming with DNA and then boosting with VLV-MHBs tended to yield a response greater than that observed for primary immunization alone (FIG. 7B). These results suggest that combining immunization strategies may induce stronger T cell responses than using VLVs alone.

Figure 7C:
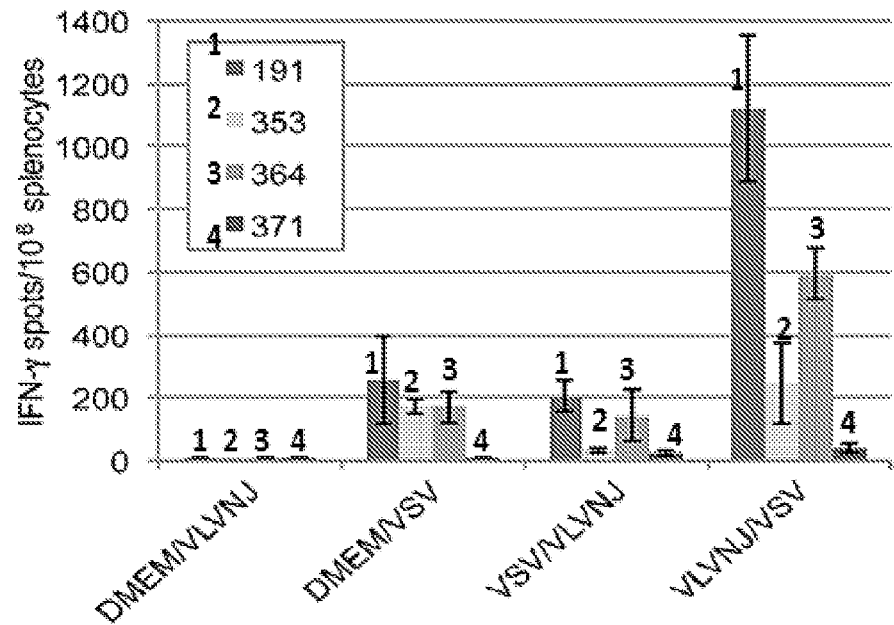

To further investigate heterologous prime-boost strategies, a prime-boost experiment combining VLV vaccination with VSV vaccination was performed. In this experiment, mice were primed and boosted with various combinations of VLV-MHBs, $VLV_{NJ}$-MHBs, or VSV-MHBs (FIG. 7C). Combining $VLV_{NJ}$-MHBs immunization with VSV-MHBs immunization led to significant increases in HBV-specific T cells. Importantly, performing a $VLV_{NJ}$-MHBs prime followed by a VSV-MHBs boost yielded T cell responses more than 3 times greater than any of the other immunization protocols. Together, these data indicate that combining heterologous immunization strategies in prime-boost protocols can lead to significant improvements in HBV-specific CD8 T cell responses.

Figure 8:
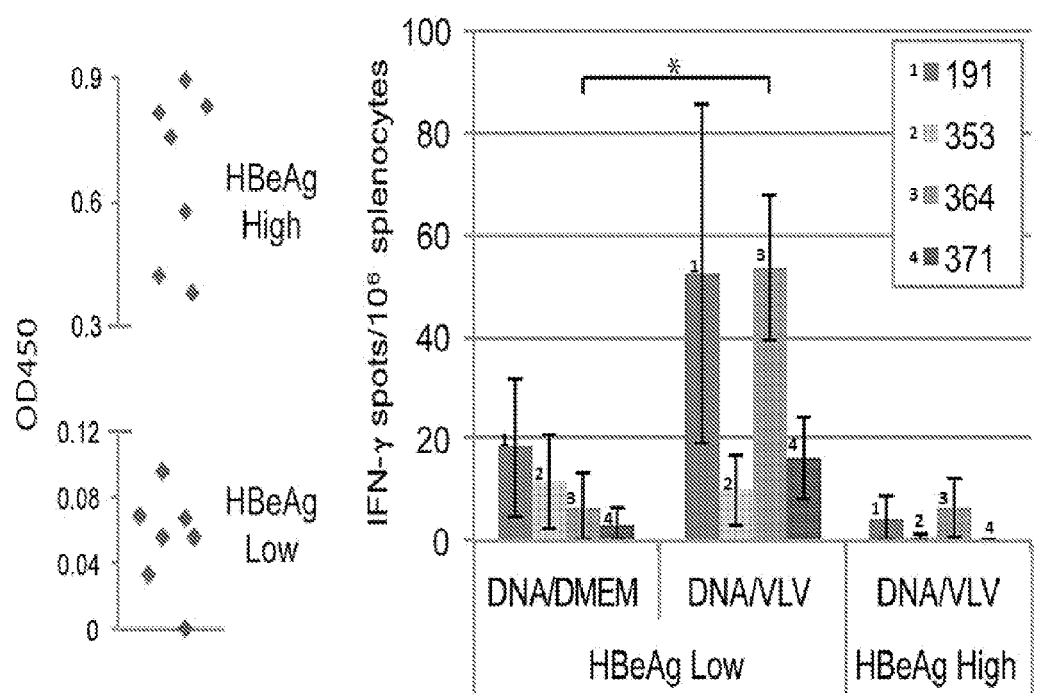
FIG. 8 is a series of graphs showing that prime-boost protocol using VLV-MHBs induces CD8 T cell responses in HBV transgenic mice. HBV 1.3 transgenic mice were screened for HBeAg expression and separated into HBeAg low (OD450<0.1) or HBeAg high (OD450>0.3) groups. All mice were primed with 50 μg pCMV-S2.S and boosted 4 wks later with DMEM (n=3) or $10^7$ IFU of VLV-MHBs (n≥4). IFN-γ ELISPOT assays were performed 1 wk post boost. Values are presented as average number of spots/$10^6$ cells of each group, error bars represent S.E. *p<0.05.

Example 9: VLV-MHBs Immunization Induces CD8 T Cell Responses in a Model of Chronic Infection In order to test the therapeutic potential of VLV-MHBs immunization, 1.3.32 HBV transgenic mice were used as a model of chronic infection. These mice express variable levels of the HBV transgene, which can be measured by serum HBeAg level (Guidotti et al., 1995, Journal of virology 69:6158-6169). HBV therapeutic vaccination can likely be used in combination with other treatment modalities such as antivirals or other immunomodulatory drugs. To model the lower antigen load that might present in a person receiving long-term antiviral therapy, $HBeAg^{low}$ mice were immunized. A single immunization with VLV-MHBs did not induce any HBV-specific immune responses. However, priming with DNA and then boosting with VLV-MHBs did induce T cell responses to at least one epitope (FIG. 8). Though immune responses were detected in $HBeAg^{low}$ mice, VLV-MHBs vaccination did not elicit T cell responses in $HBeAg^{high}$ mice. These results suggest that combination of VLV vaccination with other treatment strategies to lower antigenemia may represent a novel approach for HBV immunotherapy.

Example 10: Advantages of VLV-Based Vaccine

Compared to the currently available HBV vaccine or other potential virus-based vaccine vectors, the VLV-based vaccine has a number of advantages. These include but are not limited to: a) the potential to induce long lasting immunity in a single dose; b) the lack of pre-existing immunity to vector components in the human population; c) an increased potency for T cell generation compared to recombinant protein or DNA vaccines; d) an increased safety compared to other viral vaccine vectors; and e) a relative ease of production.

During the HBV hydrodynamic challenge, a marked reduction in HBV replication in mice immunized with VLV-MHBs was observed. However, unlike mice immunized with VSV-MHBs, no significant elevation in alanine aminotransferase (ALT) levels was observed beyond that induced by the injection. This result combined with the lack of histopathology suggests that noncytolytic mechanisms may play a significant role in clearance. Given that noncytolytic methods are an important mode of HBV clearance and that the cytolytic function of T cells can often mediate disease pathogenesis (Guidotti et al., 1996, Immunity 4:25-36; Thimme et al., 2003, Journal of virology 77:68-76), the lack of observable liver disease in VLV-MHBs immunized mice suggests that this vaccine does not induce an overly pathogenic immune response.

The aim of boosting strategies is to expand the memory T cell pool to a particular antigen. Generally during boosting, a secondary response greater than the primary response can be observed. Unexpectedly however, boosting with a serotype switch VLV construct resulted in a CD8 T cell response of similar magnitude to the primary response to VLV-MHBs (FIG. 8). One possibility for this result is that a single immunization with VLV-MHBs does not induce a memory response capable of being boosted. However, since a protection and T cell expansion at 6 weeks post immunization were observed, VLV-MHBs likely induces a durable memory response. Nevertheless, it is possible that the kinetics of memory development may not allow for optimum boosting at 4 weeks post immunization. Indeed, it is unknown how long antigen persists after VLV inoculation, a factor that can influence memory T cell development (Kaech et al., 2002, Nature reviews, Immunology 2:251-262). Alternatively, the kinetics of the secondary expansion may be such that analysis at 1 week post boost did not accurately reflect the peak response. Finally, priming with the weaker VLV ($VLV_{NJ}$-MHBs) and boosting with the more immunogenic VLV-MHBs may improve responses as this concept of delivering the less immunogenic vaccine as the prime generally strengthens prime boost vaccination approaches. Further analysis of these factors may improve or more accurately reflect the CD8 T cell response after boost.

BRIEF SUMMARY

Overall, the VLV vaccine expressing MHBs of the present invention demonstrates that a viral vaccine system, in combination with other vaccine strategies may lead to an effective HBV therapeutic. Although further optimization may benefit this vaccine strategy, investigation in other preclinical models may highlight the potential of the VLV system. Furthermore, the ability of the VLV system to induce responses in the tolerogenic environment of transgenic mice suggests that the system will likely be useful when designing vaccines for other pathogens. Indeed, VLVs have already shown promise in the HIV field (Rose et al., 2008, PNAS 105:5839-5843; Schell et al., 2011, Journal of virology 85:5764-5772). Further investigation into vaccines for other pathogens and diseases may highlight the versatility and usability of the VLV vaccine system.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Nucleotide Sequence (5'-3') of the High Titer Hybrid-Virus Vector: pCMV-SFVG-p50R (SEQ ID NO: 5)

```
5'-CTAGTGCATCCAAAGAATTCAAAAAGCTTCTCGAGAGTACTTCTAG
AGCGGCCGCGCATCGATTTTCCACCCGGGTGGGGTACCAGGTAAGTGTA
CCCAATTCGCCCTATAGTGAGTCGTATTACAATTCACTGGCCGTCGTTT
TACAACGTCGTGACTGGGAAAACCCTGGCGTTACCCAACTTAATCGCCT
TGCAGCACATCCCCCTTTCGCCAGCTGGCGTAATAGCGAAGAGGCCCGC
ACCGATCGCCCTTCCCAACAGTTGCGCAGCCTGAATGGCGAATGGAGAT
CCAATTTTTAAGTGTATAATGTGTTAAACTACTGATTCTAATTGTTTGT
GTATTTTAGATTCACAGTCCCAAGGCTCATTTCAGGCCCCTCAGTCCTC
ACAGTCTGTTCATGATCATAATCAGCCATACCACATTTGTAGAGGTTTT
ACTTGCTTTAAAAAACCTCCCACACCTCCCCCTGAACCTGAAACATAAA
ATGAATGCAATTGTTGTTGTTAACTTGTTTATTGCAGCTTATAATGGTT
ACAAATAAAGCAATAGCATCACAAATTTCACAAATAAAGCATTTTTTTC
ACTGCATTCTAGTTGTGGTTTGTCCAAACTCATCAATGTATCTTAACGC
GTAAATTGTAAGCGTTAATATTTTGTTAAAATTCGCGTTAAATTTTTGT
TAAATCAGCTCATTTTTTAACCAATAGGCCGAAATCGGCAAAATCCCTT
ATAAATCAAAAGAATAGACCGAGATAGGGTTGAGTGTTGTTCCAGTTTG
GAACAAGAGTCCACTATTAAAGAACGTGGACTCCAACGTCAAAGGGCGA
AAAACCGTCTATCAGGGCGATGGCCCACTACGTGAACCATCACCCTAAT
CAAGTTTTTTGGGGTCGAGGTGCCGTAAAGCACTAAATCGGAACCCTAA
AGGGAGCCCCCGATTTAGAGCTTGACGGGGAAAGCCGGCGAACGTGGCG
AGAAAGGAAGGGAAGAAAGCGAAAGGAGCGGGCGCTAGGGCGCTGGCAA
GTGTAGCGGTCACGCTGCGCGTAACCACCACACCCGCCGCGCTTAATGC
GCCGCTACAGGGCGCGTCAGGTGGCACTTTTCGGGGAAATGTGCGCGGA
ACCCCTATTTGTTTATTTTTCTAAATACATTCAAATATGTATCCGCTCA
TGAGACAATAACCCTGATAAATGCTTCAATAATATTGAAAAAGGAAGAG
TCCTGAGGCGGAAAGAACCAGCTGTGGAATGTGTGTCAGTTAGGGTGTG
GAAAGTCCCCAGGCTCCCCAGCAGGCAGAAGTATGCAAAGCATGCATCT
CAATTAGTCAGCAACCAGGTGTGGAAAGTCCCCAGGCTCCCCAGCAGGC
AGAAGTATGCAAAGCATGCATCTCAATTAGTCAGCAACCATAGTCCCGC
CCCTAACTCCGCCCATCCCGCCCCTAACTCCGCCCAGTTCCGCCCATTC
TCCGCCCCATGGCTGACTAATTTTTTTTATTTATGCAGAGGCCGAGGCC
GCCTCGGCCTCTGAGCTATTCCAGAAGTAGTGAGGAGGCTTTTTTGGAG
GCCTAGGCTTTTGCAAAGATCGATCAAGAGACAGGATGAGGATCGTTTC
GCATGATTGAACAAGATGGATTGCACGCAGGTTCTCCGGCCGCTTGGGT
GGAGAGGCTATTCGGCTATGACTGGGCACAACAGACAATCGGCTGCTCT
GATGCCGCCGTGTTCCGGCTGTCAGCGCAGGGGCGCCCGGTTCTTTTTG
TCAAGACCGACCTGTCCGGTGCCCTGAATGAACTGCAAGACGAGGCAGC
GCGGCTATCGTGGCTGGCCACGACGGGCGTTCCTTGCGCAGCTGTGCTC
GACGTTGTCACTGAAGCGGGAAGGGACTGGCTGCTATTGGGCGAAGTGC
CGGGGCAGGATCTCCTGTCATCTCACCTTGCTCCTGCCGAGAAAGTATC
CATCATGGCTGATGCAATGCGGCGGCTGCATACGCTTGATCCGGCTACC
TGCCCATTCGACCACCAAGCGAAACATCGCATCGAGCGAGCACGTACTC
GGATGGAAGCCGGTCTTGTCGATCAGGATGATCAAGAGCATCAGGGGCT
CGCGCCAGCCGAACTGTTCGCCAGGCTCAAGGCGAGCATGCCCGACGGC
GAGGATCTCGTCGTGACCCATGGCGATGCCTGCTTGCCGAATATCATGG
TGGAAAATGGCCGCTTTTCTGGATTCATCGACTGTGGCCGGCTGGGTGT
GGCGGACCGCTATCAGGACATAGCGTTGGCTACCCGTGATATTGCTGAA
GAGCTTGGCGGCGAATGGGCTGACCGCTTCCTCGTGCTTTACGGTATCG
CCGCTCCCGATTCGCAGCGCATCGCCTTCTATCGCCTTCTTGACGAGTT
CTTCTGAGCGGGACTCTGGGGTTCGAAATGACCGACCAAGCGACGCCCA
ACCTGCCATCACGAGATTTCGATTCCACCGCCGCCTTCTATGAAAGGTT
GGGCTTCGGAATCGTTTTCCGGGACGCCGGCTGGATGATCCTCCAGCGC
GGGGATCTCATGCTGGAGTTCTTCGCCCACCCTAGGGGGAGGCTAACTG
AAACACGGAAGGAGACAATACCGGAAGGAACCCGCGCTATGACGGCAAT
AAAAAGACAGAATAAAACGCACGGTGTTGGGTCGTTTGTTCATAAACGC
GGGGTTCGGTCCCAGGGCTGGCACTCTGTCGATACCCCACCGAGACCCC
ATTGGGGCCAATACGCCCGCGTTTCTTCCTTTTCCCCACCCCACCCCCC
AAGTTCGGGTGAAGGCCCAGGGCTCGCAGCCAACGTCGGGGCGGCAGGC
CCTGCCATAGCCTCAGGTTACTCATATATACTTTAGATTGATTTAAAAC
TTCATTTTTAATTTAAAAGGATCTAGGTGAAGATCCTTTTTGATAATCT
CATGACCAAAATCCCTTAACGTGAGTTTTCGTTCCACTGAGCGTCAGAC
CCCGTAGAAAAGATCAAAGGATCTTCTTGAGATCCTTTTTTTCTGCGCG
TAATCTGCTGCTTGCAAACAAAAAAACCACCGCTACCAGCGGTGGTTTG
TTTGCCGGATCAAGAGCTACCAACTCTTTTTCCGAAGGTAACTGGCTTC
AGCAGAGCGCAGATACCAAATACTGTCCTTCTAGTGTAGCCGTAGTTAG
```

GCCACCACTTCAAGAACTCTGTAGCACCGCCTACATACCTCGCTCTGCT

AATCCTGTTACCAGTGGCTGCTGCCAGTGGCGATAAGTCGTGTCTTACC

GGGTTGGACTCAAGACGATAGTTACCGGATAAGGCGCAGCGGTCGGGCT

GAACGGGGGGTTCGTGCACACAGCCCAGCTTGGAGCGAACGACCTACAC

CGAACTGAGATACCTACAGCGTGAGCTATGAGAAAGCGCCACGCTTCCC

GAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAG

TCCTGTCGGGTTTCGCCACCTCTGACTTGAGCGTCGATTTTTGTGATGC

TCGTCAGGGGGCGGAGCCTATGGAAAAACGCCAGCAACGCGGCCTTTT

TACGGTTCCTGGCCTTTTGCTGGCCTTTTGCTCACATGTTCTTTCCTGC

GTTATCCCTGATTCTGTGGATAACCGTATTACCGCCATGCATTAGTTA

TTAATAGTAATCAATTACGGGGTCATTAGTTCATAGCCCATATATGGAG

TTCCGCGTTACATAACTTACGGTAAATGGCCCGCCTGGCTGACCGCCCA

ACGACCCCCGCCCATTGACGTCAATAATGACGTATGTTCCCATAGTAAC

GCCAATAGGGACTTTCCATTGACGTCAATGGGTGGAGTATTTACGGTAA

ACTGCCCACTTGGCAGTACATCAAGTGTATCATATGCCAAGTACGCCCC

CTATTGACGTCAATGACGGTAAATGGCCCGCCTGGCATTATGCCCAGTA

CATGACCTTATGGGACTTTCCTACTTGGCAGTACATCTACGTATTAGTC

ATCGCTATTACCATGGTGATGCGGTTTTGGCAGTACATCAATGGGCGTG

GATAGCGGTTTGACTCACGGGGATTTCCAAGTCTCCACCCCATTGACGT

CAATGGGAGTTTGTTTTGGCACCAAAATCAACGGGACTTTCCAAAATGT

CGTAACAACTCCGCCCCATTGACGCAAATGGGCGGTAGGCGTGTACGGT

GGGAGGTCTATATAAGCAGAGCTGGTTTAGTGAACCGTATGGCGGATGT

GTGACATACACGACGCCAAAAGATTTTGTTCCAGCTCCTGCCACCTCCG

CTACGCGAGAGATTAACCACCCACGATGGCCGCCAAAGTGCATGTTGAT

ATTGAGGCTGACAGCCCATTCATCAAGTCTTTGCAGAAGGCATTTCCGT

CGTTCGAGGTGGAGTCATTGCAGGTCACACCAAATGACCATGCAAATGC

CAGAGCATTTTCGCACCTGGCTACCAAATTGATCGAGCAGGAGACTGAC

AAAGACACACTCATCTTGGATATCGGCAGTGCGCCTTCCAGGAGAATGA

TGTCTACGCACAAATACCACTGCGTATGCCCTATGCGCAGCGCAGAAGA

CCCCGAAAGGCTCGTATGCTACGCAAAGAAACTGGCAGCGGCCTCCGAG

AAGGTGCTGGATAGAGAGATCGCAGGAAAAATCACCGACCTGCAGACCG

TCATGGCTACGCCAGAGCTGAATCTCCTACCTTTTGCCTGCATACAGA

CGTCACGTGTCGTACGGCAGCCGAAGTGGCCGTATACCAGGACGTGTAT

GCTGTACATGCACCAACATCGCTGTACCATCAGGCGATGAAAGGTGTCA

GAACGGCGTATTGGATTGGGTTTGACACCACCCCGTTTATGTTTGACGC

GCTAGCAGGCGCGTATCCAACCTACGCCACAAACTGGGCCGACGAGCAG

GTGTTACAGGCCAGGAACATAGGACTGTGTGCAGCATCCTTGACTGAGG

GAAGACTCGGCAAACTGTCCATTCTCCGCAAGAAGCAATTGAAACCTTG

CGACACAGTCATGTTCTCGGTAGGATCTACATTGTACACTGAGAGCAGA

AAGCTACTGAGGAGCTGGCACTTACCCTCCGTATTCCACCTGAAAGGTA

AACAATCCTTTACCTGTAGGTGCGATACCATCGTATCATGTGAAGGGTA

CGTAGTTAAGAAAATCACTATGTGCCCCGGCCTGTACGGTAAAACGGTA

GGGTACGCCGTGACGTATCACGCGGAGGGATTCCTAGTGTGCAAGACCA

CAGACACTGTCAAAGGAGAAAGAGTCTCATTCCCTGTATGCACCTACGT

CCCCTCAACCATCTGTGATCAAATGACTGGCATACTGGCGACCGACATC

ACACCGGAGGACGCACAGAAGTTGTTAGTGGGATTGAATCAGAGGATAG

TTGTGAACGGAAGAACACAGCGAAACACTAACACGATGAAGAACTATCT

GCTTCCGATTGTGGCCGTCGCATTTAGCAAGTGGGCGAGGGAATACAAG

GCAGACCTTGATGATGAAAAACCTCTGGGTGTCCGAGAGAGGTCACTTA

CTTGCTGCTGCTTGTGGGCATTTAAAACGAGGAAGATGCACACCATGTA

CAAGAAACCAGACACCCAGACAATAGTGAAGGTGCCTTCAGAGTTTAAC

TCGTTCGTCATCCCGAGCCTATGGTCTACAGGCCTCGCAATCCCAGTCA

GATCACGCATTAAGATGCTTTTGGCCAAGAAGACCAAGCGAGAGTCAAT

ACCTGTTCTCGACGCGTCGTCAGCCAGGGATGCTGAACAAGAGGAGAAG

GAGAGGTTGGAGGCCGAGCTGACTAGAGAAGCCTTACCACCCCTCGTCC

CCACCGCGCCGGCGGAGACGGGAGTCGTCGACGTCGACGTTGAAGAACT

AGAGTATCACGCAGGTGCAGGGGTCGTGGAAACACCTCGCAGCGCGTTG

AAAGTCACCGCACAGCCGAACGGCGTACTACTAGGAAATTACGTAGTTC

TGTCCCCGCAGACCGTGCTCAAGAGCTCCAAGTTGGCCCCCGTGCACCC

TCTAGCAGAGCAGGTGAAAATAATAACACATAACGGGAGGGCCGGCCGT

TACCAGGTCGACGGATATGACGGCAGGGTCCTACTACCATGTGGATCGG

CCATTCCGGTCCCTGAGTTTCAAGCTTTGAGCGAGAGCGCCACTATGGT

GTACAACGAAAGGGAGTTCGTCAACAGGAAACTATACCATATTGCCGTT

CACGGACCGTCGCTGAACACCGACGAGGAGAACTACGAGAAAGTCAGAG

CTGAAAGAACTGACGCCGAGTACGTGTTCGACGTAGATAAAAAATGCTG

CGTCAAGAGAGAGGAAGCGTCGGGTTTGGTGTTGGTGGGAGAGCTAACC

AACCCCCCGTTCCATGAATTCGCCTACGAAGGGCTGAAGATCAGGCCGT

CGGCACCATATAAGACTACAGTAGTAGGAGTCTTTGGGGTTCCGGGATC

AGGCAAGTCTGCTATTATTAAGAGCCTCGTGACCAAACACGATCTGGTC

ACCAGCGGCAAGAAGGAGAACTGCCAGGAAATAGTCAACGACGTGAAGA

AGCACCGCGGACTGGACATCCAGGCAAAAACAGTGGACTCCATCCTGCT

AAACGGGTGTCGTCGTGCCGTGGACATCCTATATGTGGACGAGGCTTTC

GCTTGCCATTCCGGTACTCTGCTAGCCCTAATTGCTCTTGTTAAACCTC

GGAGCAAAGTGGTGTTATGCGGAGACCCCAAGCAATGCGGATTCTTCAA

TATGATGCAGCTTAAGGTGAACTTCAACCACAACATCTGCACTGAAGTA

TGTCATAAAAGTATATCCAGACGTTGCACGCGTCCAGTCACGGCCATCG

TGTCTACATTGCACTACGGAGGCAAGATGCGCACGACCAACCCGTGCAA

CAAACCCTATAATCATAGACACCACAGGACAGACCAAGCCCAAGCCAGGA

GACATCGTGTTAACATGCTTCCGAGGCTGGGTAAAGCAGCTGCAGTTGG

ACTACCGTGGACACGAAGTCATGACAGCAGCAGCATCTCAGGGCCTCAC

CCGCAAAGGGGTATACGCCGTAAGGCAGAAGGTGAATGAAAATCCCTTG

TATGCCCCTGCGTCGGAGCACGTGAATGTACTGCTGACGCGCACTGAGG

ATAGGCTGGTGTGGAAAACGCTGGCCGGCGATCCCTGGATTAAGGTCCT

ATCAAACATTCCACAGGGTAACTTTACGGCCACATTGGAAGAATGGCAA

GAAGAACACGACAAAATAATGAAGGTGATTGAAGGACCGGCTGCGCCTG

TGGACGCGTTCCAGAACAAAGCGAACGTGTGTTGGGCGAAAAGCCTGGT

GCCTGTCCTGGACACTGCCGGAATCAGATTGACAGCAGAGGAGTGGAGC

ACCATAATTACAGCATTTAAGGAGGACAGAGCTTACTCTCCAGTGGTGG

CCTTGAATGAAATTTGCACCAAGTACTATGGAGTTGACCTGGACAGTGG

CCTGTTTTCTGCCCCGAAGGTGTCCCTGTATTACGAGAACAACCACTGG

GATAACAGACCTGGTGGAAGGATGTATGGATTCAATGCCGCAACAGCTG

CCAGGCTGGAAGCTAGACATACCTTCCTGAAGGGGCAGTGGCATACGGG

CAAGCAGGCAGTTATCGCAGAAAGAAAAATCCAACCGCTTTCTGTGCTG

GACAATGTAATTCCTATCAACCGCAGGCTGCCGCACGCCCTGGTGACTG

AGTACAAGACGGTTAAAGGCAGTAGGGTTGAGTGGCTGGTCAATAAAGT

AAGAGGGTACCACGTCCTGCTGGTGAGTGAGTACAACCTGGCTTTGCCT

CGACGCAGGGTCACTTGGTTGTCACCGCTGAATGTCACAGGCGCCGATA

GGTGCTACGACCTAAGTTTAGGACTGCCGGCTGACGCCGGCAGGTTCGA

CTTGGTCTTTGTGAACATTCACACGGAATTCAGAATCCACCACTACCAG

CAGTGTGTCGACCACGCCATGAAGCTGCAGATGCTTGGGGGAGATGCGC

TACGACTGCTAAAACCCGGCGGCAGCCTCTTGATGAGAGCTTACGGATA

CGCCGATAAAATCAGCGAAGCCGTTGTTTCCTCCTTAAGCAGAAAGTTC

TCGTCTGCAAGAGTGTTGCGCCCGGATTGTGTCACCAGCAATACAGAAG

TGTTCTTGCTGTTCTCCAACTTTGACAACGGAAAGAGACCCTCTACGCT

ACACCAGATGAATACCAAGCTGAGTGCCGTGTATGCCGGAGAAGCCATG

CACACGGCCGGGTGTGCACCATCCTACAGAGTTAAGAGAGCAGACATAG

CCACGTGCACAGAAGCGGCTGTGTGGTTAACGCAGCTAACGCCCGTGGAAC

TGTAGGGGATGGCGTATGCAGGGCCGTGGCGAAGAAATGGCCGTCAGCC

TTTAAGGGAGAAGCAACACCAGTGGGCACAATTAAAACAGTCATGTGCG

GCTCGTACCCCGTCATCCACGCTGTAGCGCCTAATTTCTCTGCCACGAC

TGAAGCGGAAGGGGACCGCGAATTGGCCGCTGTCTACCGGGCAGTGGCC

GCCGAAGTAAACAGACTGTCACTGAGCAGCGTAGCCATCCCGCTGCTGT

CCACAGGAGTGTTCAGCGGCGGAAGAGATAGGCTGCAGCAATCCCTCAA

CCATCTATTCACAGCAATGGACGCCACGGACGCTGACGTGACCATCTAC

TGCAGAGACAAAAGTTGGGAGAAGAAAATCCAGGAAGCCATAGACACGA

GGACGGCTGTGGAGTTGCTCAATGATGACGTGGAGCTGACCACAGACTT

GGTGAGAGTGCACCCGGACAGCAGCCTGGTGGGTCGTAAGGGCTACAGT

ACCACTGACGGGTCGCTGTACTCGTACTTTGAAGGTACGAAATTCAACC

AGGCTGCTATTGATATGGCAGAGATACTGACGTTGTGGCCCAGACTGCA

AGAGGCAAACGAACAGATATGCCTATACGCGCTGGGCGAAACAATGGAC

AACATCAGATCCAAATGTCCGGTGAACGATTCCGATTCATCAACACCTC

CCAGGACAGTGCCCTGCCTGTGCCGCTACGCAATGACAGCAGAACGGAT

CACCCGCCTTAGGTCACACCAAGTTAAAAGCATGGTGGTTTGCTCATCT

TTTCCCCTCCCGAAATACCATGTAGATGGGGTGCAGAAGGTAAAGTGCG

AGAAGGTTCTCCTGTTCGACCCGACGGTACCTTCAGTGGTTAGTCCGCG

GAAGTATGCCGCATCTACGACGGACCACTCAGATCGGTCGTTACGAGGG

TTTGACTTGGACTGGACCACCGACTCGTCTTCCACTGCCAGCGATACCA

TGTCGCTACCCAGTTTGCAGTCGTGTGACATCGACTCGATCTACGAGCC

AATGGCTCCCATAGTAGTGACGGCTGACGTACACCCTGAACCCGCAGGC

ATCGCGGACCTGGCGGCAGATGTGCATCCTGAACCCGCAGACCATGTGG

ACCTCGAGAACCCGATTCCTCCACCGCGCCCGAAGAGAGCTGCATACCT

TGCCTCCCGCGCGGCGGAGCGACCGGTGCCGGCGCCGAGAAAGCCGACG

CCTGCCCCAAGGACTGCGTTTAGGAACAAGCTGCCTTTGACGTTCGGCG

ACTTTGACGAGCACGAGGTCGATGCGTTGGCCTCCGGGATTACTTTCGG

AGACTTCGACGACGTCCTGCGACTAGGCCGCGCGGGTGCATATATTTTC

TCCTCGGACACTGGCAGCGGACATTTACAACAAAAATCCGTTAGGCAGC

ACAATCTCCAGTGCGCACAACTGGATGCGGTCGAGGAGGAGAAAATGTA

CCCGCCAAAATTGGATACTGAGAGGGAGAAGCTGTTGCTGCTGAAAATG

CAGATGCACCCATCGGAGGCTAATAAGAGTCGATACCAGTCTCGCAAAG

TGGAGAACATGAAAGCCACGGTGGTGGACAGGCTCACATCGGGGGCCAG

ATTGTACACGGGAGCGGACGTAGGCCGCATACCAACATACGCGGTTCGG

TACCCCCGCCCCGTGTACTCCCCTACCGTGATCGAAAGATTCTCAAGCC

CCGATGTAGCAATCGCAGCGTGCAACGAATACCTATCCAGAAATTACCC

AACAGTGGCGTCGTACCAGATAACAGATGAATACGACGCATACTTGGAC

ATGGTTGACGGGTCGGATAGTTGCTTGGACAGAGCGACATTCTGCCCGG

CGAAGCTCCGGTGCTACCCGAAACATCATGCGTACCACCAGCCGACTGT

ACGCAGTGCCGTCCCGTCACCCTTTCAGAACACACTACAGAGCGTGCTA

GCGGCCGCCACCAAGAGAAACTGCAACGTCACGCAAATGCGAGAACTAC

CCACCATGGACTCGGCAGTGTTCAACGTGGAGTGCTTCAAGCGCTATGC

CTGCTCCGGAGAATATTGGGAAGAATATGCTAAACAACCTATCCGGATA

ACCACTGAGAACATCACTACCTATGTGACCAAATTGAAAGGCCCGAAAG

CTGCTGCCTTGTTCGCTAAGACCCACAACTTGGTTCCGCTGCAGGAGGT

TCCCATGGACAGATTCACGGTCGACATGAAACGAGATGTCAAAGTCACT

CCAGGGACGAAACACACAGAGGAAAGACCCAAAGTCCAGGTAATTCAAG

CAGCGGAGCCATTGGCGACCGCTTACCTGTGCGGCATCCACAGGGAATT

AGTAAGGAGACTAAATGCTGTGTTACGCCCTAACGTGCACACATTGTTT

GATATGTCGGCCGAAGACTTTGACGCGATCATCGCCTCTCACTTCCACC

CAGGAGACCCGGTTCTAGAGACGGACATTGCATCATTCGACAAAAGCCA

GGACGACTCCTTGGCTCTTACAGGTTTAATGATCCTCGAAGATCTAGGG

GTGGATCAGTACCTGCTGGACTTGATCGAGGCAGCCTTTGGGGAAATAT

CCAGCTGTCACCTACCAACTGGCACGCGCTTCAAGTTCGGAGCTATGAT

GAAATCGGGCATGTTTCTGACTTTGTTTATTAACACTGTTTTGAACATC
ACCATAGCAAGCAGGGTACTGGAGCAGAGACTCACTGACTCCGCCTGTG
CGGCCTTCATCGGCGACGACAACATCGTTCACGGAGTGATCTCCGACAA
GCTGATGCGGAGAGGTGCGCGTCGTGGGTCAACATGGAGGTGAAGATC
ATTGACGCTGTCATGGGCGAAAAACCCCCATATTTTTGTGGGGGATTCA
TAGTTTTTGACAGCGTCACACAGACCGCCTGCCGTGTTTCAGACCCACT
TAAGCGCCTGTTCAAGTTGGGTAAGCCGCTAACAGCTGAAGACAAGCAG
GACGAAGACAGGCGACGAGCACTGAGTGACGAGGTTAGCAAGTGGTTCC
GGACAGGCTTGGGGGCCGAACTGGAGGTGGCACTAACATCTAGGTATAA
GGTAGAGGGCTGCAAAAGTATCCTCATAGCCATGGCCACCTTGGCGAGG
GACATTAAGGCGTTTAAGAAATTGAGAGGACCTGTTATACACCTCTACG
GCGGTCCTAGATTGGTGCGTTAATACACAGAATTCTGATTGGATCCTCG
AGGAATTCTGACACTATGAAGTGCCTTTTGTACTTAGCCTTTTTATTCA
TTGGGGTGAATTGCAAGTTCACCATAGTTTTTCCACACAACCAAAAAGG
AAACTGGAAAAATGTTCCTTCTAATTACCATTATTGCCCGTCAAGCTCA
GATTTAAATTGGCATGATGACTTAATAGGCACAGCCTTACAAGTCAAAA
TGCCCAAGAGTCACAAGGCTATTCAAGCAGACGGTTGGATGTGTCATGC
TTCCAAATGGGTCACTACTTGTGACTTCCGCTGGTATGGACCGAAGTAT
ATAACACATTCCATCCGATCCTTCACTCCATCTGTAGAACAATGCAAGG
AAAGCATTGAACAAACGAAACAAGGAACTTGGCTGAATCCAGGCTTCCC
TCCTCAAAGTTGTGGATATGCAACTGTGACGGATGCCGAAGCAGTGATT
GTCCAGGTGACTCCTCACCATGTGCTGGTTGATGAATACACAGGAGAAT
GGGTTGATTCACAGTTCATCAACGGAAAATGCAGCAATTACATATGCCC
CACTGTCCATAACTCTACAACCTGGCATTCTGACTATAAGGTCAAAGGG
CTATGTGATTCTAACCTCATTTCCATGGACATCACCTTCTTCTCAGAGG

ACGGAGAGCTATCATCCCTGGGAAAGGAGGGCACAGGGTTCAGAAGTAA
CTACTTTGCTTATGAAACTGGAGGCAAGGCCTGCAAAATGCAATACTGC
AAGCATTGGGGAGTCAGACTCCCATCAGGTGTCTGGTTCGAGATGGCTG
ATAAGGATCTCTTTGCTGCAGCCAGATTCCCTGAATGCCCAGAAGGGTC
AAGTATCTCTGCTCCATCTCAGACCTCAGTGGATGTAAGTCTAATTCAG
GACGTTGAGAGGATCTTGGATTATTCCCTCTGCCAAGAAACCTGGAGCA
AAATCAGAGCGGGTCTTCCAATCTCTCCAGTGGATCTCAGCTATCTTGC
TCCTAAAAACCCAGGAACCGGTCCTGCTTTCACCATAATCAATGGTACC
CTAAAATACTTTGAGACCAGATACATCAGAGTCGATATTGCTGCTCCAA
TCCTCTCAAGAATGGTCGGAATGATCAGTGGAACTACCACAGAAAGGGA
ACTGTGGGATGACTGGGCACCATATGAAGACGTGGAAATTGGACCCAAT
GGAGTTCTGAGGACCAGTTCAGGATATAAGTTTCCTTTATACATGATTG
GACATGGTATGTTGGACTCCGATCTTCATCTTAGCTCAAAGGCTCAGGT
GTTCGAACATCCTCACATTCAAGACGCTGCTTCGCAACTTCCTGATGAT
GAGAGTTTATTTTTGGTGATACTGGGCTATCCAAAAATCCAATCGAGC
TTGTAGAAGGTTGGTTCAGTAGTTGGAAAAGCTCTATTGCCTCTTTTTT
CTTTATCATAGGGTTAATCATTGGACTATTCTTGGTTCTCCGAGTTGGT
ATCCATCTTTGCATTAAATTAAAGCACACCAAGAAAAGACAGATTTATA
CAGACATAGAGATGAACCGACTTGGAAAGTAACTCAAATCCTGCACAAC
AGATTCTTCATGTTTGGACCAAATCAACTTGTGATACCATGCTCAAAGA
GGCCTCAAACCATAACTGTATAACTTGTAACAAAGCGCAACAAGACCTG
CGCAATTGGCCCCGTGGTCCGCCTCACGGAAACTCGGGGCAACTCATAT
TGACACATTAATTGGCAATAATTGGAAGCTTACATAAGCTTAATTCGAC
GAATAATTGGATTTTTATTTTATTTTGCAATTGGTTTTTAATATTTCCA
AAAAAAAAAAAAAAAAAAAAAAAAAAAAAAAAAAAAAAAAAAAAAAAA
AAAAAAAAAAAAAAAAAAA-3'

What is claimed:

1. A high titer hybrid-hepatitis B virus (HBV) vector comprising a DNA sequence comprising a promoter sequence operably linked to a DNA sequence encoding Semliki Forest virus (SFV) non-structural protein nucleotide sequences, operably linked to an SFV subgenomic RNA promoter, operably linked to DNA encoding an HBV antigen or fragment thereof, operably linked to a 2A DNA encoding a 2A peptide, which is in turn operably linked to a vesicular stomatitis virus (VSV) G DNA encoding a VSV G protein, wherein the SFV non-structural protein nucleotide sequences comprise at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C, wherein the vector lacks nucleotide sequences which encode SFV structural proteins, further wherein when the vector is propagated in cell culture, titers of at least $10^7$ plaque forming units (pfu) per ml of virus like vesicles (VLVs) are obtained.

2. The high titer hybrid-HBV vector of claim 1, wherein the promoter sequence comprises a constitutive promoter.

3. The high titer hybrid-HBV vector of claim 2, wherein the promoter sequence comprises the cytomegalovirus immediate early promoter.

4. The high titer hybrid-HBV vector of claim 1, wherein titers of at least $5\times10^7$ pfu/ml of VLVs are obtained.

5. The high titer hybrid-HBV vector of claim 4, wherein titers of at least $1\times10^8$ pfu/ml of VLVs are obtained.

6. The high titer hybrid-HBV vector of claim 1, wherein the HBV antigen or fragment thereof is selected from the group consisting of Hepatitis B surface antigen (HBsAg), Hepatitis B core antigen (HBcAg), Hepatitis B e antigen (HBeAg), Hepatitis B viral protein X (HBx), Hepatitis B virus DNA polymerase, and any combination thereof.

7. The HBV antigen of claim 6, wherein the Hepatitis B surface antigen (HBsAg) is the middle hepatitis B surface (MHBs) protein.

8. A composition comprising virus like vesicles (VLVs) produced by the high titer hybrid-virus vector of claim 1.

9. The composition of claim 8, wherein the HBV antigen or fragment thereof is selected from the group consisting of Hepatitis B surface antigen (HBsAg), Hepatitis B core antigen (HBcAg), Hepatitis B e antigen (HBeAg), Hepatitis B viral protein X (HBx), Hepatitis B virus DNA polymerase, and any combination thereof.

10. The HBV antigen of claim 9, wherein the Hepatitis B surface antigen (HBsAg) is the middle hepatitis B surface (MHBs) protein.

11. The composition of claim 8, wherein the HBV antigen is associated with hepatitis B virus (HBV) infection.

12. A method of immunizing a subject against HBV infection, the method comprising administering to the subject a composition comprising at least $10^7$ pfu/ml of the VLVs of claim 8, wherein expression of the HBV antigen induces an immune response in the subject.

13. The method of claim 12, wherein the HBV antigen or fragment thereof is selected from the group consisting of Hepatitis B surface antigen (HBsAg), Hepatitis B core antigen (HBcAg), Hepatitis B e antigen (HBeAg), Hepatitis B viral protein X (HBx), Hepatitis B virus DNA polymerase and any combination thereof.

14. A method of treating and/or preventing a disease in a subject, the method comprising administering a therapeutically effective amount of the composition of claim 8 to a subject in need of such treatment.

15. The method of claim 14, wherein the disease is a hepatitis B virus (HBV) infection.

16. The method of claim 15, wherein the HBV infection is a chronic infection.

17. A method of vaccinating a subject, the method comprising administering to the subject a pharmaceutically acceptable amount of the composition of claim 8, wherein administration of the composition elicits an immune response in the subject.

18. The method of claim 17, wherein the composition is a prophylactic vaccine.

19. The method of claim 18, wherein the composition is a therapeutic vaccine.

20. The method of claim 17, wherein the composition is administered in combination with an adjuvant.

21. The method of claim 20, wherein the adjuvant is selected from the group consisting of Freund's complete adjuvant, Freund's incomplete adjuvant, Quil A, Detox, ISCOMs and squalene.

22. A method of generating a memory T cell immune response to a HBV antigen or fragment thereof in a subject the method comprising the steps of: (a) administering the composition of claim 8 to a subject in an amount effective to elicit an immune response in the subject; (b) administering a second effective amount of the composition of claim 8 at a second, subsequent time period, wherein T memory cells directed against the HBV antigen or fragment thereof are generated in the subject.

23. A method of generating an adaptive B cell immune response to a HBV antigen or fragment thereof in a subject the method comprising the steps of: (a) administering the composition of claim 8 to a subject in an amount effective to elicit an immune response in the subject; (b) administering a second effective amount of the composition of claim 8 at a second, subsequent time period, wherein B memory cells directed against the HBV antigen or fragment thereof are generated in the subject.

24. The method of any of claims 12, 14, 17, 22 and 23, wherein the subject is a mammal.

25. The method of claim 24, wherein the mammal is a human.

26. A high titer hybrid-hepatitis B virus (HBV) vector comprising a DNA sequence comprising a promoter sequence operably linked to a DNA sequence encoding alphavirus non-structural protein nucleotide sequences, operably linked to an alphavirus subgenomic RNA promoter, operably linked to DNA encoding an HBV antigen or fragment thereof, operably linked to a 2A DNA encoding a 2A peptide, which is in turn operably linked to a vesicular stomatitis virus (VSV) G DNA encoding a VSV G protein, wherein the alphavirus non-structural protein nucleotide sequences comprise at least two of the mutations selected from the group consisting of G-4700-A, A-5424-G, G-5434-A, T-5825-C, T-5930-C, A-6047-G, G-6783-A, G-6963-A, G-7834-A, T-8859-A, T-8864-C, G-9211-A, A-10427-G, G-11560-A, A-11871-G and T-11978-C, wherein the vector lacks nucleotide sequences which encode alphavirus structural proteins, further wherein when the vector is propagated in cell culture, titers of at least $10^7$ plaque forming units (pfu) per ml of virus like vesicles (VLVs) are obtained.

* * * * *

SEQUENCE LISTING

<160> NUMBER OF SEQ ID NOS: 9

<210> SEQ ID NO 1
<211> LENGTH: 44
<212> TYPE: DNA
<213> ORGANISM: Artificial Sequence
<220> FEATURE:
<223> OTHER INFORMATION: Primer

<400> SEQUENCE: 1
gatcgatctt aattaaaatg gacatcgacc cttataaaga tttg         44

<210> SEQ ID NO 2
<211> LENGTH: 42
<212> TYPE: DNA
<213> ORGANISM: Artificial Sequence
<220> FEATURE:
<223> OTHER INFORMATION: Primer

<400> SEQUENCE: 2

```
gatcgatccc tgcaggacat tgagattccc gagattgaga tc                    42

<210> SEQ ID NO 3
<211> LENGTH: 41
<212> TYPE: DNA
<213> ORGANISM: Artificial Sequence
<220> FEATURE:
<223> OTHER INFORMATION: Primer

<400> SEQUENCE: 3
gatcgatctt aattaaaatg cagtggaatt ccacaacctt c                     41

<210> SEQ ID NO 4
<211> LENGTH: 45
<212> TYPE: DNA
<213> ORGANISM: Artificial Sequence
<220> FEATURE:
<223> OTHER INFORMATION: Primer

<400> SEQUENCE: 4
gatcgatccc tgcaggaatg tatacccaaa gacaaaagaa aattg                 45

<210> SEQ ID NO 5
<211> LENGTH: 13590
<212> TYPE: DNA
<213> ORGANISM: Artificial Sequence
<220> FEATURE:
<223> OTHER INFORMATION: Hybrid-virus vector (pCMV-SFVG-p50R)

<400> SEQUENCE: 5
ctagtgcatc caaagaattc aaaaagcttc tcgagagtac ttctagagcg gccgcgcatc   60
gattttccac ccgggtgggg taccaggtaa gtgtacccaa ttcgccctat agtgagtcgt  120
attacaattc actggccgtc gttttacaac gtcgtgactg ggaaaaccct ggcgttaccc  180
aacttaatcg ccttgcagca catccccctt tcgccagctg gcgtaatagc gaagaggccc  240
gcaccgatcg cccttcccaa cagttgcgca gcctgaatgg cgaatggaga tccaattttt  300
aagtgtataa tgtgttaaac tactgattct aattgtttgt gtattttaga ttcacagtcc  360
caaggctcat ttcaggcccc tcagtcctca cagtctgttc atgatcataa tcagccatac  420
cacatttgta gaggttttac ttgctttaaa aaacctccca cacctccccc tgaacctgaa  480
acataaaatg aatgcaattg ttgttgttaa cttgtttatt gcagcttata atggttacaa  540
ataaagcaat agcatcacaa atttcacaaa taaagcattt ttttcactgc attctagttg  600
tggtttgtcc aaactcatca atgtatctta acgcgtaaat tgtaagcgtt aatattttgt  660
taaaattcgc gttaaatttt tgttaaatca gctcattttt taaccaatag gccgaaatcg  720
gcaaaatccc ttataaatca aaagaataga ccgagatagg gttgagtgtt gttccagttt  780
ggaacaagag tccactatta agaacgtgga ctccaacgt caagggcga aaaccgtct    840 atcagggcga tggcccacta cgtgaaccat cacctaatc aagttttttg gggtcgaggt   900
gccgtaaagc actaaatcgg aaccctaaag ggagccccg atttagagct tgacggggaa    960
agccggcgaa cgtggcgaga aggaaggga agaaagcgaa aggagcgggc gctagggcgc  1020
tggcaagtgt agcggtcacg ctgcgcgtaa ccaccacacc cgccgcgctt aatgcgccgc  1080
tacagggcgc gtcaggtggc acttttcggg gaaatgtgcg cggaacccct atttgtttat  1140
ttttctaaat acattcaaat atgtatccgc tcatgagaca ataaccctga taatgcttc   1200 aataatattg aaaaaggaag agtcctgagg cggaaagaac cagctgtgga atgtgtgtca  1260
gttagggtgt ggaaagtccc caggctcccc agcaggcaga agtatgcaaa gcatgcatct  1320
```

```
caattagtca gcaaccaggt gtggaaagtc cccaggctcc ccagcaggca gaagtatgca      1380
aagcatgcat ctcaattagt cagcaaccat agtcccgccc ctaactccgc ccatcccgcc      1440
cctaactccg cccagttccg cccattctcc gccccatggc tgactaattt ttttttattta    1500 tgcagaggcc gaggccgcct cggcctctga gctattccag aagtagtgag gaggcttttt      1560
tggaggccta ggcttttgca aagatcgatc aagagacagg atgaggatcg tttcgcatga     1620
ttgaacaaga tggattgcac gcaggttctc cggccgcttg ggtggagagg ctattcggct     1680
atgactgggc acaacagaca atcggctgct ctgatgccgc cgtgttccgg ctgtcagcgc     1740
aggggcgccc ggttcttttt gtcaagaccg acctgtccgg tgccctgaat gaactgcaag     1800
acgaggcagc gcggctatcg tggctggcca cgacgggcgt tccttgcgca gctgtgctcg     1860
acgttgtcac tgaagcggga agggactggc tgctattggg cgaagtgccg gggcaggatc     1920
tcctgtcatc tcaccttgct cctgccgaga agtatccat catggctgat gcaatgcggc      1980
ggctgcatac gcttgatccg gctacctgcc cattcgacca ccaagcgaaa catcgcatcg     2040
agcgagcacg tactcggatg aagccggtc ttgtcgatca ggatgatcaa gagcatcagg      2100
ggctcgcgcc agccgaactg ttcgccaggc tcaaggcgag catgcccgac ggcgaggatc     2160
tcgtcgtgac ccatggcgat gcctgcttgc cgaatatcat ggtggaaaat ggccgctttt    2220
ctggattcat cgactgtggc cggctgggtg tggcggaccg ctatcaggac atagcgttgg     2280
ctacccgtga tattgctgaa gagcttggcg gcgaatgggc tgaccgcttc ctcgtgcttt     2340
acggtatcgc cgctcccgat tcgcagcgca tcgccttcta tcgccttctt gacgagttct    2400
tctgagcggg actctggggt tcgaaatgac cgaccaagcg acgcccaacc tgccatcacg     2460
agatttcgat tccaccgccg ccttctatga aggttgggc ttcggaatcg ttttccggga     2520
cgccggctgg atgatcctcc agcgcgggga tctcatgctg gagttcttcg cccaccctag     2580
ggggaggcta actgaaacac ggaaggagac aataccggaa ggaacccgcg ctatgacggc     2640
aataaaaaga cagaataaaa cgcacggtgt tgggtcgttt gttcataaac gcggggttcg     2700
gtcccagggc tggcactctg tcgataccc accgagaccc cattgggcc aatacgcccg      2760 cgtttcttcc ttttccccac cccaccccc aagttcgggt gaaggccag ggctcgcagc      2820 caacgtcggg gcggcaggcc ctgccatagc ctcaggttac tcatatatac tttagattga     2880
tttaaaactt cattttaat ttaaaaggat ctaggtgaag atccttttg ataatctcat      2940 gaccaaaatc ccttaacgtg agttttcgtt ccactgagcg tcagacccg tagaaaagat     3000 caaaggatct tcttgagatc cttttttct gcgcgtaatc tgctgcttgc aaacaaaaaa     3060
accaccgcta ccagcggtgg tttgtttgcc ggatcaagag ctaccaactc ttttttccgaa    3120 ggtaactggc ttcagcagag cgcagatacc aaatactgtc cttctagtgt agccgtagtt    3180
aggccaccac ttcaagaact ctgtagcacc gcctacatac ctcgctctgc taatcctgtt    3240
accagtggct gctgccagtg gcgataagtc gtgtcttacc gggttggact caagacgata    3300
gttaccggat aaggcgcagc ggtcgggctg aacggggggt tcgtgcacac agcccagctt    3360
ggagcgaacg acctacaccg aactgagata cctacagcgt gagctatgag aaagcgccac    3420
gcttcccgaa gggagaaagg cggacaggta tccggtaagc ggcagggtcg gaacaggaga    3480
gcgcacgagg gagcttccag ggggaaacgc ctggtatctt tatagtcctg tcgggtttcg    3540
ccacctctga cttgagcgtc gatttttgtg atgctcgtca gggggcgga gcctatggaa     3600 aaacgccagc aacgcggcct ttttacggtt cctggccttt tgctggcctt ttgctcacat    3660
```

```
gttctttcct gcgttatccc ctgattctgt ggataaccgt attaccgcca tgcattagtt    3720
attaatagta atcaattacg gggtcattag ttcatagccc atatatggag ttccgcgtta    3780
cataacttac ggtaaatggc ccgcctggct gaccgcccaa cgaccccgc ccattgacgt     3840 caataatgac gtatgttccc atagtaacgc caatagggac tttccattga cgtcaatggg    3900
tggagtattt acggtaaact gcccacttgg cagtacatca agtgtatcat atgccaagta    3960
cgccccctat tgacgtcaat gacggtaaat ggcccgcctg gcattatgcc cagtacatga    4020
ccttatggga ctttcctact tggcagtaca tctacgtatt agtcatcgct attaccatgg    4080
tgatgcggtt ttggcagtac atcaatgggc gtggatagcg gtttgactca cggggatttc    4140
caagtctcca ccccattgac gtcaatggga gtttgttttg gcaccaaaat caacgggact    4200
ttccaaaatg tcgtaacaac tccgccccat tgacgcaaat gggcggtagg cgtgtacggt    4260
gggaggtcta tataagcaga gctggtttag tgaaccgtat ggcggatgtg tgacatacac    4320
gacgccaaaa gattttgttc cagctcctgc cacctccgct acgcgagaga ttaaccaccc    4380
acgatggccg ccaaagtgca tgttgatatt gaggctgaca gcccattcat caagtctttg    4440
cagaaggcat ttccgtcgtt cgaggtggag tcattgcagg tcacaccaaa tgaccatgca    4500
aatgccagag cattttcgca cctggctacc aaattgatcg agcaggagac tgacaaagac    4560
acactcatct ggatatcgg cagtgcgcct tccaggagaa tgatgtctac gcacaaatac     4620
cactgcgtat gccctatgcg cagcgcagaa gaccccgaaa ggctcgtatg ctacgcaaag    4680
aaactggcag cggcctccga gaaggtgctg gatagagaga tcgcaggaaa aatcaccgac    4740
ctgcagaccg tcatggctac gccagacgct gaatctccta ccttttgcct gcatacagac    4800
gtcacgtgtc gtacggcagc cgaagtggcc gtataccagg acgtgtatgc tgtacatgca    4860
ccaacatcgc tgtaccatca ggcgatgaaa ggtgtcagaa cggcgtattg gattgggttt    4920
gacaccaccc cgtttatgtt tgacgcgcta gcaggcgcgt atccaaccta cgccacaaac    4980
tgggccgacg agcaggtgtt acaggccagg aacataggac tgtgtgcagc atccttgact    5040
gagggaagac tcggcaaact gtccattctc cgcaagaagc aattgaaacc ttgcgacaca    5100
gtcatgttct cggtaggatc tacattgtac actgagagca gaaagctact gaggagctgg    5160
cacttaccct ccgtattcca cctgaaaggt aaacaatcct ttacctgtag gtgcgatacc    5220
atcgtatcat gtgaagggta cgtagttaag aaaatcacta tgtgccccgg cctgtacggt    5280
aaaacggtag ggtacgccgt gacgtatcac gcggagggat tcctagtgtg caagaccaca    5340
gacactgtca aaggagaaag agtctcattc cctgtatgca cctacgtccc ctcaaccatc    5400
tgtgatcaaa tgactggcat actggcgacc gacatcacac cggaggacgc acagaagttg    5460
ttagtgggat tgaatcagag gatagttgtg aacggaagaa cacagcgaaa cactaacacg    5520
atgaagaact atctgcttcc gattgtggcc gtcgcattta gcaagtgggc gagggaatac    5580
aaggcagacc ttgatgatga aaaacctctg ggtgtccgag agaggtcact tacttgctgc    5640
tgcttgtggg catttaaaac gaggaagatg cacaccatgt acaagaaacc agacacccag    5700
acaatagtga aggtgccttc agagtttaac tcgttcgtca tcccgagcct atggtctaca    5760
ggcctcgcaa tccagtcag atcacgcatt aagatgcttt tggccaagaa gaccaagcga    5820
gagtcaatac ctgttctcga cgcgtcgtca gccagggatg ctgaacaaga ggagaaggag    5880
aggttggagg ccgagctgac tagagaagcc ttaccacccc tcgtcccac cgcgccggcg     5940 gagacgggag tcgtcgacgt cgacgttgaa gaactagagt atcacgcagg tgcagggctc    6000
gtggaaacac ctcgcagcgc gttgaaagtc accgcacagc cgaacggcgt actactagga    6060
```

| | |
|---|---|
| aattacgtag ttctgtcccc gcagaccgtg ctcaagagct ccaagttggc ccccgtgcac | 6120 |
| cctctagcag agcaggtgaa aataataaca cataacggga gggccggccg ttaccaggtc | 6180 |
| gacggatatg acggcagggt cctactacca tgtggatcgg ccattccggt ccctgagttt | 6240 |
| caagctttga gcgagagcgc cactatggtg tacaacgaaa gggagttcgt caacaggaaa | 6300 |
| ctataccata ttgccgttca cggaccgtcg ctgaacaccg acgaggagaa ctacgagaaa | 6360 |
| gtcagagctg aaagaactga cgccgagtac gtgttcgacg tagataaaaa atgctgcgtc | 6420 |
| aagagagagg aagcgtcggg tttggtgttg gtgggagagc taaccaaccc cccgttccat | 6480 |
| gaattcgcct acgaagggct gaagatcagg ccgtcggcac catataagac tacagtagta | 6540 |
| ggagtctttg gggttccggg atcaggcaag tctgctatta ttaagagcct cgtgaccaaa | 6600 |
| cacgatctgg tcaccagcgg caagaaggag aactgccagg aaatagtcaa cgacgtgaag | 6660 |
| aagcaccgcg gactggacat ccaggcaaaa acagtggact ccatcctgct aaacgggtgt | 6720 |
| cgtcgtgccg tggacatcct atatgtggac gaggctttcg cttgccattc cggtactctg | 6780 |
| ctagccctaa ttgctcttgt taaacctcgg agcaaagtgg tgttatgcgg agaccccaag | 6840 |
| caatgcggat tcttcaatat gatgcagctt aaggtgaact tcaaccacaa catctgcact | 6900 |
| gaagtatgtc ataaaagtat atccagacgt tgcacgcgtc cagtcacggc catcgtgtct | 6960 |
| acattgcact acgaggcaa gatgcgcacg accaacccgt gcaacaaacc cataatcata | 7020 |
| gacaccacag acagaccaa gcccaagcca ggagacatcg tgttaacatg cttccgaggc | 7080 |
| tgggtaaagc agctgcagtt ggactaccgt ggacacgaag tcatgacagc agcagcatct | 7140 |
| cagggcctca cccgcaaagg ggtatacgcc gtaaggcaga aggtgaatga aaatccctty | 7200 |
| tatgcccctg cgtcggagca cgtgaatgta ctgctgacgc gcactgagga taggctggtg | 7260 |
| tggaaaacgc tggccggcga tccctggatt aaggtcctat caaacattcc acagggtaac | 7320 |
| tttacggcca cattggaaga atggcaagaa gaacacgaca aaataatgaa ggtgattgaa | 7380 |
| ggaccggctg cgcctgtgga cgcgttccag aacaaagcga acgtgtgttg ggcgaaaagc | 7440 |
| ctggtgcctg tcctggacac tgccggaatc agattgacag cagaggagtg gagcaccata | 7500 |
| attacagcat ttaaggagga cagagcttac tctccagtgg tggccttgaa tgaaatttgc | 7560 |
| accaagtact atggagttga cctggacagt ggcctgtttt ctgccccgaa ggtgtccctg | 7620 |
| tattacgaga caaccactg ggataacaga cctggtggaa ggatgtatgg attcaatgcc | 7680 |
| gcaacagctg ccaggctgga agctagacat accttcctga aggggcagtg catacgggc | 7740 |
| aagcaggcag ttatcgcaga aagaaaaatc caaccgcttt ctgtgctgga caatgtaatt | 7800 |
| cctatcaacc gcaggctgcc gcacgccctg gtgactgagt acaagacggt taaaggcagt | 7860 |
| agggttgagt ggctggtcaa taagtaaga gggtaccacg tcctgctggt gagtgagtac | 7920 |
| aacctggctt tgcctcgacg cagggtcact tggttgtcac cgctgaatgt cacaggcgcc | 7980 |
| gataggtgct acgacctaag tttaggactg ccggctgacg ccggcaggtt cgacttggtc | 8040 |
| tttgtgaaca ttcacacgga attcagaatc caccactacc agcagtgtgt cgaccacgcc | 8100 |
| atgaagctgc agatgcttgg gggagatgcg ctacgactgc taaaacccgg cggcagcctc | 8160 |
| ttgatgagag cttacggata cgccgataaa atcagcgaag ccgttgtttc ctccttaagc | 8220 |
| agaaagttct cgtctgcaag agtgttgcgc ccggattgtg tcaccagcaa tacagaagtg | 8280 |
| ttcttgctgt tctccaactt tgacaacgga aagagaccct ctacgctaca ccagatgaat | 8340 |
| accaagctga gtgccgtgta tgccggagaa gccatgcaca cggccgggtg tgcaccatcc | 8400 |

```
tacagagtta agagagcaga catagccacg tgcacagaag cggctgtggt taacgcagct    8460
aacgcccgtg gaactgtagg ggatggcgta tgcaggccg tggcgaagaa atggccgtca     8520
gcctttaagg gagaagcaac accagtgggc acaattaaaa cagtcatgtg cggctcgtac    8580
cccgtcatcc acgctgtagc gcctaatttc tctgccacga ctgaagcgga aggggaccgc   8640
gaattggccg ctgtctaccg ggcagtggcc gccgaagtaa acagactgtc actgagcagc    8700
gtagccatcc cgctgctgtc cacaggagtg ttcagcggcg aagagatag gctgcagcaa    8760
tccctcaacc atctattcac agcaatggac gccacggacg ctgacgtgac catctactgc   8820
agagacaaaa gttgggagaa gaaaatccag gaagccatag acacgaggac ggctgtggag   8880
ttgctcaatg atgacgtgga gctgaccaca gacttggtga gagtgcaccc ggacagcagc   8940
ctggtgggtc gtaagggcta cagtaccact gacgggtcgc tgtactcgta ctttgaaggt   9000
acgaaattca accaggctgc tattgatatg gcagagatac tgacgttgtg gcccagactg    9060
caagaggcaa acgaacagat atgcctatac gcgctgggcg aaacaatgga caacatcaga   9120
tccaaatgtc cggtgaacga ttccgattca tcaacacctc ccaggacagt gccctgcctg   9180
tgccgctacg caatgacagc agaacggatc cccgccctta ggtcacacca agttaaaagc   9240
atggtggttt gctcatcttt tccctcccg aaataccatg tagatggggt gcagaaggta   9300
aagtgcgaga aggttctcct gttcgacccg acggtacctt cagtggttag tccgcggaag   9360
tatgccgcat ctacgacgga ccactcagat cggtcgttac gagggtttga cttggactgg   9420
accaccgact cgtcttccac tgccagcgat accatgtcgc tacccagttt gcagtcgtgt   9480
gacatcgact cgatctacga gccaatggct cccatagtag tgacggctga cgtacaccct    9540
gaacccgcag gcatcgcgga cctggcggca gatgtgcatc ctgaacccgc agaccatgtg   9600
gacctcgaga acccgattcc tccaccgcgc ccgaagagag ctgcatacct tgcctcccgc   9660
gcggcggagc gaccggtgcc ggcgccgaga agccgacgc ctgccccaag gactgcgttt    9720
aggaacaagc tgcctttgac gttcggcgac tttgacgagc acgaggtcga tgcgttggcc   9780
tccgggatta ctttcggaga cttcgacgac gtcctgcgac taggccgcgc gggtgcatat   9840
attttctcct cggacactgg cagcggacat ttacaacaaa aatccgttag gcagcacaat   9900
ctccagtgcg cacaactgga tgcggtcgag gaggagaaaa tgtacccgcc aaaattggat    9960
actgagaggg agaagctgtt gctgctgaaa atgcagatgc acccatcgga ggctaataag  10020
agtcgatacc agtctcgcaa agtggagaac atgaaagcca cggtggtgga caggctcaca  10080
tcggggggcca gattgtacac gggagcggac gtaggccgca taccaacata cgcggttcgg  10140
tacccccgcc ccgtgtactc ccctaccgtg atcgaaagat tctcaagccc cgatgtagca  10200
atcgcagcgt gcaacgaata cctatccaga aattacccaa cagtggcgtc gtaccagata  10260
acagatgaat acgacgcata cttggacatg gttgacgggt cggatagttg cttggacaga  10320
gcgacattct gcccggcgaa gctccggtgc taccggaaac atcatgcgta ccaccagccg  10380
actgtacgca gtgccgtccc gtcacccttt cagaacacac tacagagcgt gctagcggcc  10440
gccaccaaga gaaactgcaa cgtcacgcaa atgcgagaac tacccaccat ggactcggca  10500
gtgttcaacg tggagtgctt caagcgctat gcctgctccg gagaatattg gaagaatat   10560
gctaaacaac ctatccggat aaccactgag aacatcacta cctatgtgac caaattgaaa  10620
ggcccgaaag ctgctgcctt gttcgctaag acccacaact tggttccgct gcaggaggtt  10680
cccatggaca gattcacggt cgacatgaaa cgagatgtca agtcactcc agggacgaaa  10740
cacacagagg aaagacccaa agtccaggta attcaagcag cggagccatt ggcgaccgct  10800
```

```
tacctgtgcg gcatccacag ggaattagta aggagactaa atgctgtgtt acgccctaac   10860
gtgcacacat tgtttgatat gtcggccgaa gactttgacg cgatcatcgc ctctcacttc   10920
cacccaggag acccggttct agagacggac attgcatcat tcgacaaaag ccaggacgac   10980
tccttggctc ttacaggttt aatgatcctc gaagatctag gggtggatca gtacctgctg   11040
gacttgatcg aggcagcctt tggggaaata tccagctgtc acctaccaac tggcacgcgc   11100
ttcaagttcg gagctatgat gaaatcgggc atgtttctga ctttgtttat taacactgtt   11160
ttgaacatca ccatagcaag cagggtactg gagcagagac tcactgactc cgcctgtgcg   11220
gccttcatcg gcgacgacaa catcgttcac ggagtgatct ccgacaagct gatggcggag   11280
aggtgcgcgt cgtgggtcaa catggaggtg aagatcattg acgctgtcat gggcgaaaaa   11340
cccccatatt tttgtggggg attcatagtt tttgacagcg tcacacagac cgcctgccgt   11400
gtttcagacc cacttaagcg cctgttcaag ttgggtaagc cgctaacagc tgaagacaag   11460
caggacgaag acaggcgacg agcactgagt gacgaggtta gcaagtggtt ccggacaggc   11520
ttgggggccg aactggaggt ggcactaaca tctaggtata aggtagaggg ctgcaaaagt   11580
atcctcatag ccatggccac cttggcgagg acattaagg cgtttaagaa attgagagga   11640
cctgttatac acctctacgg cggtcctaga ttggtgcgtt aatacacaga attctgattg   11700
gatcctcgag gaattctgac actatgaagt gccttttgta cttagccttt ttattcattg   11760
gggtgaattg caagttcacc atagtttttc cacacaacca aaaggaaac tggaaaaatg    11820 ttccttctaa ttaccattat tgcccgtcaa gctcagattt aaattggcat gatgacttaa   11880
taggcacagc cttacaagtc aaaatgccca agagtcacaa ggctattcaa gcagacggtt   11940
ggatgtgtca tgcttccaaa tgggtcacta cttgtgactt ccgctggtat ggaccgaagt   12000
atataacaca ttccatccga tccttcactc catctgtaga acaatgcaag gaaagcattg   12060
aacaaacgaa acaaggaact tggctgaatc caggcttccc tcctcaaagt tgtggatatg   12120
caactgtgac ggatgccgaa gcagtgattg tccaggtgac tcctcaccat gtgctggttg   12180
atgaatacac aggagaatgg gttgattcac agttcatcaa cggaaaatgc agcaattaca   12240
tatgccccac tgtccataac tctacaacct ggcattctga ctataaggtc aaagggctat   12300
gtgattctaa cctcattttc catggacatca ccttcttctc agaggacgga gagctatcat   12360
ccctgggaaa ggagggcaca gggttcagaa gtaactactt tgcttatgaa actggaggca   12420
aggcctgcaa aatgcaatac tgcaagcatt ggggagtcag actcccatca ggtgtctggt   12480
tcgagatggc tgataaggat ctctttgctg cagccagatt ccctgaatgc ccagaagggt   12540
caagtatctc tgctccatct cagacctcag tggatgtaag tctaattcag gacgttgaga   12600
ggatcttgga ttattccctc tgccaagaaa cctggagcaa atcagagcg ggtcttccaa    12660 tctctccagt ggatctcagc tatcttgctc ctaaaaaccc aggaaccggt cctgctttca   12720
ccataatcaa tggtaccta aaatactttg agaccagata catcagagtc gatattgctg   12780
ctccaatcct ctcaagaatg gtcggaatga tcagtggaac taccacagaa agggaactgt   12840
gggatgactg ggcaccatat gaagacgtgg aaattggacc caatgagtt ctgaggacca   12900 gttcaggata taagtttcct ttatacatga ttggacatgg tatgttggac tccgatcttc   12960
atcttagctc aaaggctcag gtgttcgaac atcctcacat tcaagacgct gcttcgcaac   13020
ttcctgatga tgagagttta ttttttggtg atactgggct atccaaaaat ccaatcgagc   13080
ttgtagaagg ttggttcagt agttggaaaa gctctattgc ctctttttc tttatcatag   13140
```

```
ggttaatcat tggactattc ttggttctcc gagttggtat ccatctttgc attaaattaa    13200
agcacaccaa gaaaagacag atttatacag acatagagat gaaccgactt ggaaagtaac    13260
tcaaatcctg cacaacagat tcttcatgtt tggaccaaat caacttgtga taccatgctc    13320
aaagaggcct caaaccataa ctgtataact tgtaacaaag cgcaacaaga cctgcgcaat    13380
tggccccgtg gtccgcctca cggaaactcg ggcaactca  tattgacaca ttaattggca    13440
ataattggaa gcttacataa gcttaattcg acgaataatt ggatttttat tttattttgc    13500
aattggtttt taatatttcc aaaaaaaaaa aaaaaaaaaa aaaaaaaaaa aaaaaaaaaa    13560
aaaaaaaaaa aaaaaaaaaa aaaaaaaaaa                                    13590

<210> SEQ ID NO 6
<211> LENGTH: 862
<212> TYPE: DNA
<213> ORGANISM: Hepatitis B virus

<400> SEQUENCE: 6
ttaattaaaa tgcagtggaa ttccacaacc ttccaccaaa ctctgcaaga tcccagagtg      60
agaggcctgt atttccctgc tggtggctcc agttcaggaa cagtaaaccc tgttctgact     120
actgcctctc ccttatcgtc aatcttctcg aggattgggg accctgcgct gaacatggag     180
aacatcacat caggattcct aggacccctt ctcgtgttac aggcggggtt tttcttgttg     240
acaagaatcc tcacaatacc gcagagtcta gactcgtggt ggacttctct caattttcta     300
gggggaacta ccgtgtgtct tggccaaaat tcgcagtccc caacctccaa tcactcacca     360
acctcttgtc ctccaacttg tcctggttat cgctggatgt gtctgcggcg ttttatcatc     420
ttcctcttca tcctgctgct atgcctcatc ttcttgttgg ttcttctgga ctatcaaggt     480
atgttgcccg tttgtcctct aattccagga tcctcaacaa ccagcacggg accatgccgg     540
acctgcatga ctactgctca aggaacctct atgtatccct cctgttgctg taccaaacct     600
tcggacggaa attgcacctg tattcccatc ccatcatcct gggctttcgg aaaattccta     660
tgggagtggg cctcagcccg tttctcctgg ctcagtttac tagtgccatt tgttcagtgg     720
ttcgtagggc tttcccccac tgtttggctt tcagttatat ggatgatgtg gtattggggg     780
ccaagtctgt acagcatctt gagtcccttt ttaccgctgt taccaatttt cttttgtctt     840
tgggtataca ttcctgcagg ag                                             862

<210> SEQ ID NO 7
<211> LENGTH: 568
<212> TYPE: DNA
<213> ORGANISM: Hepatitis B virus

<400> SEQUENCE: 7
ttaattaaaa tggacatcga cccttataaa gaatttggag ctactgtgga gttactctcg      60
tttttgcctt ctgacttctt tccttcagta cgagatcttc tagataccgc ctcagctctg     120
tatcgggaag ccttagagtc tcctgagcat tgttcacctc accatactgc actcaggcaa     180
gcaattcttt gctgggggga actaatgact ctagctacct gggtgggtgt taatttggaa     240
gatccagcgt ctagagacct agtagtcagt tatgtcaaca ctaatatggg cctaaagttc     300
aggcaactct tgtggtttca catttcttgt ctcacttttg gaagagaaac agttatagag     360
tatttggtgt ctttcggagt gtggattcgc actcctccag cttatagacc accaaatgcc     420
cctatcctat caacacttcc ggagactact gttgttagac gacgaggcag gtcccctaga     480
agaagaactc cctcgcctcg cagacgaagg tctcaatcgc cgcgtcgcag aagatctcaa     540
```
tctcgggaat ctcaatgtcc tgcaggag                                          568

<210> SEQ ID NO 8
<211> LENGTH: 281
<212> TYPE: PRT
<213> ORGANISM: Hepatitis B virus

<400> SEQUENCE: 8

Met Gln Trp Asn Ser Thr Thr Phe His Gln Thr Leu Gln Asp Pro Arg
1               5                   10                  15

Val Arg Gly Leu Tyr Phe Pro Ala Gly Gly Ser Ser Ser Gly Thr Val
            20                  25                  30

Asn Pro Val Leu Thr Thr Ala Ser Pro Leu Ser Ser Ile Phe Ser Arg
        35                  40                  45

Ile Gly Asp Pro Ala Leu Asn Met Glu Asn Ile Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Thr Thr Val Cys Leu Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Ser Leu Tyr Ser Ile Leu Ser Pro Phe Leu Pro Leu Leu Pro
            260                 265                 270

Ile Phe Phe Cys Leu Trp Val Tyr Ile
        275                 280

<210> SEQ ID NO 9
<211> LENGTH: 183
<212> TYPE: PRT
<213> ORGANISM: Hepatitis B virus

<400> SEQUENCE: 9

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

-continued

```
Thr Ala Ser Ala Leu Tyr Arg Glu Ala Leu Glu Ser Pro Glu His Cys
        35              40              45

Ser Pro His His Thr Ala Leu Arg Gln Ala Ile Leu Cys Trp Gly Glu
    50              55              60

Leu Met Thr Leu Ala Thr Trp Val Gly Val Asn Leu Glu Asp Pro Ala
65              70              75              80

Ser Arg Asp Leu Val Val Ser Tyr Val Asn Thr Asn Met Gly Leu Lys
            85              90              95

Phe Arg Gln Leu Leu Trp Phe His Ile Ser Cys Leu Thr Phe Gly Arg
            100             105             110

Glu Thr Val Ile Glu Tyr Leu Val Ser Phe Gly Val Trp Ile Arg Thr
        115             120             125

Pro Pro Ala Tyr Arg Pro Pro Asn Ala Pro Ile Leu Ser Thr Leu Pro
        130             135             140

Glu Thr Thr Val Val Arg Arg Arg Gly Arg Ser Pro Arg Arg Arg Thr
145             150             155             160

Pro Ser Pro Arg Arg Arg Arg Ser Gln Ser Pro Arg Arg Arg Arg Ser
            165             170             175

Gln Ser Arg Glu Ser Gln Cys
            180
```

UNITED STATES PATENT AND TRADEMARK OFFICE
CERTIFICATE OF CORRECTION

PATENT NO. : 9,987,353 B2
APPLICATION NO. : 15/305180
DATED : June 5, 2018
INVENTOR(S) : Michael Robek, John Rose and Tracy Reynolds Page 1 of 1

It is certified that error appears in the above-identified patent and that said Letters Patent is hereby corrected as shown below:

On the Title Page

Item (71), Applicants: "Yale University, New Haven, CT (US); Sandra E. Osborne, Granbury, TX (US)" should be changed to -- Yale University, New Haven, CT (US) --

Signed and Sealed this
Fourth Day of June, 2019

Andrei Iancu
*Director of the United States Patent and Trademark Office*

UNITED STATES PATENT AND TRADEMARK OFFICE
CERTIFICATE OF CORRECTION

PATENT NO. : 9,987,353 B2
APPLICATION NO. : 15/305180
DATED : June 5, 2018
INVENTOR(S) : Michael Robek, John Rose and Tracy Reynolds It is certified that error appears in the above-identified patent and that said Letters Patent is hereby corrected as shown below:

In the Specification

On Column 1, Lines 18-24, please replace the existing paragraph with the following paragraph:
-- STATEMENT REGARDING FEDERALLY SPONSORED RESEARCH OR DEVELOPMENT
This invention was made with government support under AI045510 and AI040357 awarded by National Institutes of Health. The government has certain rights in the invention. --

Signed and Sealed this
Fourth Day of August, 2020

Andrei Iancu
*Director of the United States Patent and Trademark Office*